(12) United States Patent
Oliver et al.

(10) Patent No.: US 6,958,040 B2
(45) Date of Patent: Oct. 25, 2005

(54) MULTI-RESONANT ULTRASONIC CATHETER

(75) Inventors: Leonard R. Oliver, Seattle, WA (US); Richard R. Wilson, Seattle, WA (US)

(73) Assignee: Ekos Corporation, Bothell, WA (US)

(*) Notice: Subject to any disclaimer, the term of this patent is extended or adjusted under 35 U.S.C. 154(b) by 108 days.

(21) Appl. No.: 10/331,439

(22) Filed: Dec. 27, 2002

(65) Prior Publication Data

US 2004/0073114 A1 Apr. 15, 2004

Related U.S. Application Data

(60) Provisional application No. 60/344,423, filed on Dec. 28, 2001, provisional application No. 60/344,421, filed on Dec. 28, 2001.

(51) Int. Cl.[7] .............................................. A61B 8/00
(52) U.S. Cl. ...................................... 600/439; 600/459
(58) Field of Search ............................... 600/437–472; 73/625, 626; 601/2, 3; 604/22; 607/22; 128/898, 128/916

(56) References Cited

U.S. PATENT DOCUMENTS

| | | | |
|---|---|---|---|
| 4,948,587 A | 8/1990 | Kost et al. | |
| 4,951,677 A | * 8/1990 | Crowley et al. | ............ 600/463 |
| 5,059,851 A | 10/1991 | Corl et al. | |
| 5,158,071 A | 10/1992 | Umemura et al. | |
| 5,197,946 A | 3/1993 | Tachibana | |
| 5,226,421 A | 7/1993 | Frisbie et al. | |
| 5,269,291 A | 12/1993 | Carter | |
| 5,271,406 A | 12/1993 | Ganguly et al. | |
| 5,318,014 A | 6/1994 | Carter | |
| 5,345,940 A | 9/1994 | Seward et al. | |
| 5,362,309 A | 11/1994 | Carter | |
| 5,368,036 A | 11/1994 | Tanaka et al. | |
| 5,380,273 A | 1/1995 | Dubrul et al. | |
| 5,431,663 A | 7/1995 | Carter | |
| 5,447,509 A | 9/1995 | Mills et al. | |
| 5,447,510 A | 9/1995 | Jensen | |
| 5,456,259 A | 10/1995 | Barlow et al. | |
| 5,474,531 A | 12/1995 | Carter | |
| 5,523,058 A | 6/1996 | Umemura et al. | |
| 5,569,197 A | 10/1996 | Helmus et al. | |
| 5,588,432 A | 12/1996 | Crowley | |

(Continued)

FOREIGN PATENT DOCUMENTS

JP H02-180275 7/1990

(Continued)

*Primary Examiner*—Ali Imam
(74) *Attorney, Agent, or Firm*—Knobbe, Martens, Olson & Bear LLP

(57) ABSTRACT

A catheter system for delivering ultrasonic energy and a therapeutic compound to a treatment site within a patient's vasculature comprises a tubular body. The tubular body has a proximal end, a distal end and an energy delivery section positioned between the proximal end and the distal end. The catheter system further comprises an inner core configured for insertion into the tubular body. The inner core has an outer surface and comprises an electrically conductive core material. The catheter system further comprises a plurality of ultrasound radiating members positioned on the outer surface of the inner core. The ultrasound radiating members are electrically connected to the electrically conductive core material. The catheter system further comprises an electrically conductive tube-shaped member disposed over the inner core and over the ultrasound radiating members positioned thereon. At least a portion of the electrically conductive tube-shaped member is electrically connected to a plurality of the ultrasound radiating members. The catheter system further comprises control circuitry configured to deliver an input signal to a plurality of the ultrasound radiating members.

27 Claims, 21 Drawing Sheets

U.S. PATENT DOCUMENTS

| | | |
|---|---|---|
| 5,620,479 A | 4/1997 | Diederich |
| 5,628,728 A | 5/1997 | Tachibana et al. |
| 5,630,837 A | 5/1997 | Crowley |
| 5,713,831 A | 2/1998 | Olsson |
| 5,713,848 A | 2/1998 | Dubrul et al. |
| 5,735,811 A | 4/1998 | Brisken |
| 5,836,896 A | 11/1998 | Rosenschein |
| 5,916,192 A | 6/1999 | Nita et al. |
| 5,931,805 A | 8/1999 | Brisken |
| 5,957,941 A | 9/1999 | Ream |
| 5,997,497 A | 12/1999 | Nita et al. |
| 6,001,069 A | 12/1999 | Tachibana et al. |
| 6,004,269 A | 12/1999 | Crowley et al. |
| 6,024,718 A | 2/2000 | Chen et al. |
| 6,096,000 A | 8/2000 | Tachibana et al. |
| 6,110,314 A | 8/2000 | Nix et al. |
| 6,113,546 A | 9/2000 | Suorsa et al. |
| 6,113,558 A | 9/2000 | Rosenschein et al. |
| 6,117,101 A | 9/2000 | Diederich et al. |
| 6,120,454 A | 9/2000 | Suorsa et al. |
| 6,135,971 A | 10/2000 | Hutchinson et al. |
| 6,176,842 B1 | 1/2001 | Tachibana et al. |
| 6,210,356 B1 | 4/2001 | Anderson et al. |
| 6,228,046 B1 | 5/2001 | Brisken |
| 6,238,347 B1 | 5/2001 | Nix et al. |
| 6,287,271 B1 | 9/2001 | Dubrul et al. |
| 6,296,619 B1 | 10/2001 | Brisken et al. |
| 6,361,500 B1 | 3/2002 | Masters |
| 6,372,498 B2 | 4/2002 | Newman et al. |
| 6,391,042 B1 | 5/2002 | Cimino |
| 6,437,487 B1 | 8/2002 | Mohr, III et al. |
| 6,456,863 B1 | 9/2002 | Levin et al. |
| 6,508,775 B2 | 1/2003 | McKenzie et al. |
| 6,562,021 B1 | 5/2003 | Derbin et al. |
| 6,585,763 B1 | 7/2003 | Keilman et al. |
| 6,723,063 B1 | 4/2004 | Zhang et al. |
| 2001/0007861 A1 | 7/2001 | Newman et al. |
| 2001/0007940 A1 | 7/2001 | Tu et al. |
| 2001/0041880 A1 | 11/2001 | Brisken et al. |
| 2002/0000763 A1 | 1/2002 | Jones |
| 2002/0032394 A1 | 3/2002 | Brisken et al. |
| 2002/0087083 A1 | 7/2002 | Nix et al. |
| 2002/0099292 A1 | 7/2002 | Brisken et al. |
| 2002/0188276 A1 | 12/2002 | Evans et al |
| 2003/0135262 A1 | 7/2003 | Dretler et al. |
| 2004/0019318 A1 | 1/2004 | Wilson et al. |
| 2004/0024347 A1 | 2/2004 | Wilson, et al. |
| 2004/0049148 A1 | 3/2004 | Rodriguez et al. |

FOREIGN PATENT DOCUMENTS

| | | |
|---|---|---|
| WO | WO 95/26777 | 12/1995 |
| WO | WO 97/19645 | 5/1997 |
| WO | WO 00/69341 | 11/2000 |

\* cited by examiner

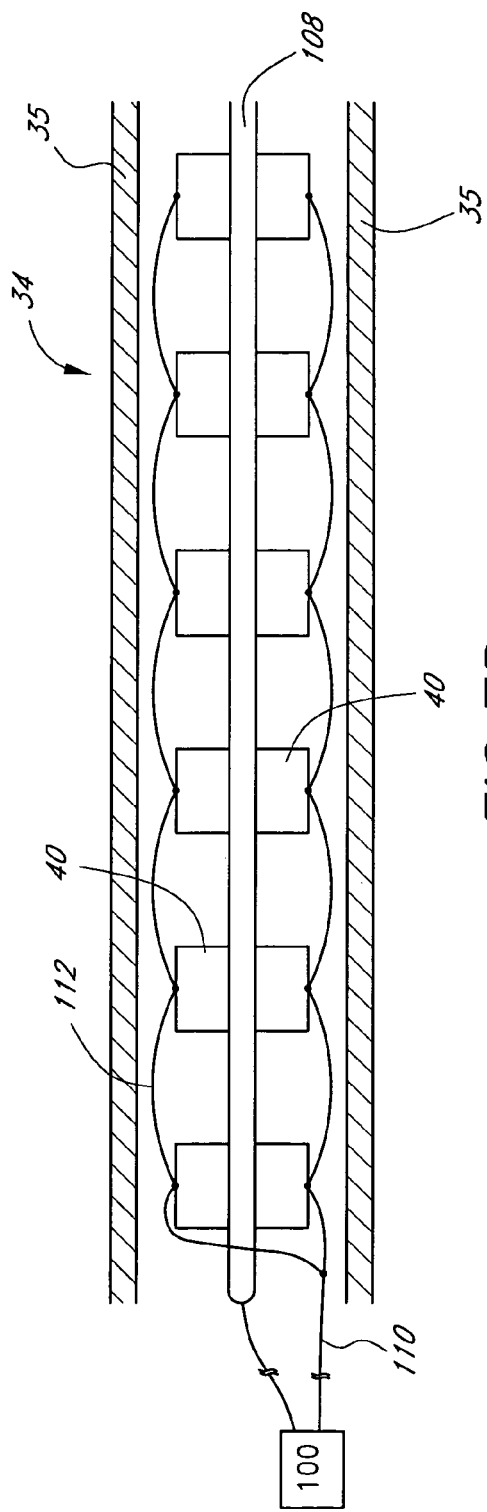
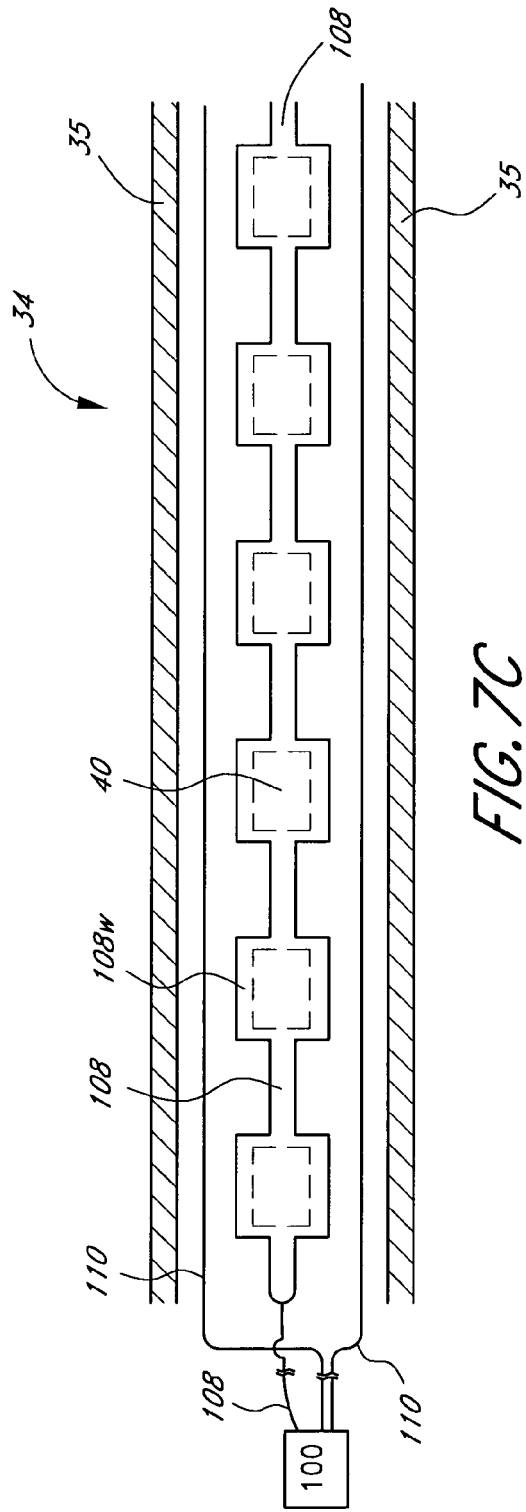

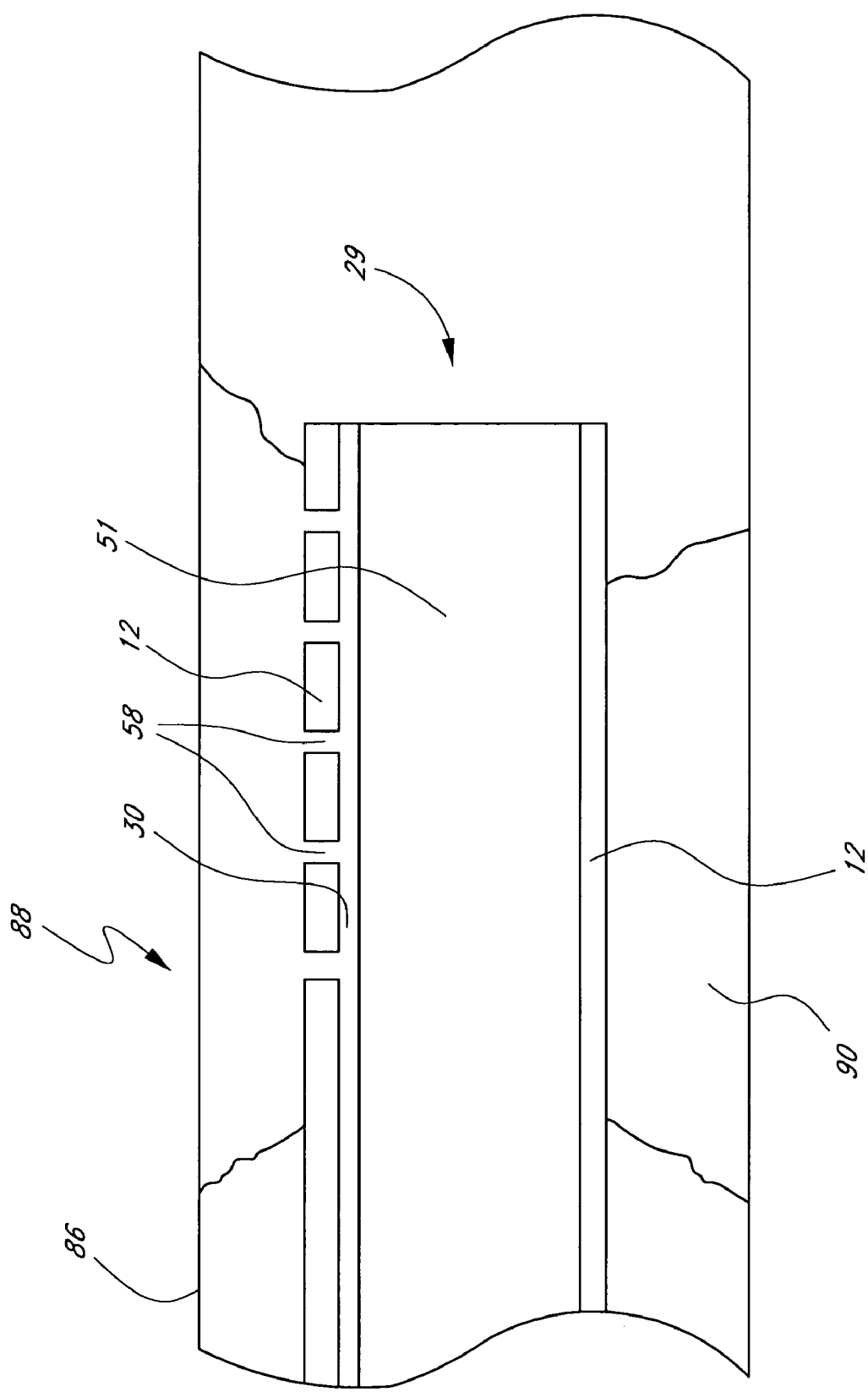

MULTI-RESONANT ULTRASONIC CATHETER

PRIORITY APPLICATION

This application claims priority under 35 U.S.C. § 119(e) from U.S. Provisional Patent Application Ser. No. 60/344,423, entitled "Multi-Resonant Catheter" and filed Dec. 28, 2001; and U.S. Provisional Patent Application Ser. No. 60/344,421, entitled "High Density Ultrasonic Element Catheter" and filed Dec. 28, 2001. The entire disclosure of both of these priority documents is hereby incorporated by reference in its entirety.

BACKGROUND OF THE INVENTION

1. Field of the Invention

The preferred embodiments of the present invention relate to an ultrasonic catheter configured to deliver ultrasonic energy and a therapeutic compound to a treatment site.

2. Description of the Related Art

Several medical applications use ultrasonic energy. For example, U.S. Pat. Nos. 4,821,740, 4,953,565 and 5,007,438 disclose the use of ultrasonic energy to enhance the effect of various therapeutic compounds. An ultrasonic catheter can be used to deliver ultrasonic energy and a therapeutic compound to a treatment site in a patient's body. Such an ultrasonic catheter typically includes an ultrasound assembly configured to generate ultrasonic energy and a fluid delivery lumen for delivering the therapeutic compound to the treatment site.

As taught in U.S. Pat. No. 6,001,069, such ultrasonic catheters can be used to treat human blood vessels that have become partially or completely occluded by plaque, thrombi, emboli or other substances that reduce the blood carrying capacity of the vessel. To remove or reduce the occlusion, the ultrasonic catheter is used to deliver solutions containing dissolution compounds directly to the occlusion site. Ultrasonic energy generated by the ultrasound assembly enhances the therapeutic effect of the dissolution compounds. For example, in one application of such an ultrasonic catheter, an ultrasound-enhanced thrombolytic therapy dissolves blood clots in arteries and veins in the treatment of diseases such as peripheral arterial occlusion or deep vein thrombosis. In such applications, ultrasonic energy enhances thrombolysis with agents such as urokinase, tissue plasminogen activator ("TPA") and the like.

Ultrasonic catheters can also be used to enhance gene therapy at a treatment site within the patient's body. For example, U.S. Pat. No. 6,135,976 discloses an ultrasonic catheter having one or more expandable sections capable of occluding a section of a body lumen, such as a blood vessel. A gene therapy composition is then delivered to the occluded vessel through the catheter fluid delivery lumen. Ultrasonic energy generated by the ultrasound assembly is applied to the occluded vessel, thereby enhancing the delivery of a genetic composition into the cells of the occluded vessel.

Ultrasonic catheters can also be used to enhance delivery and activation of light activated drugs. For example, U.S. Pat. No. 6,176,842 discloses methods for using an ultrasonic catheter to treat biological tissues by delivering a light activated drug to the biological tissues and exposing the light activated drug to ultrasonic energy.

SUMMARY OF THE INVENTION

One method for providing ultrasonically-enhanced delivery of therapeutic compounds is to provide an ultrasonic catheter with a plurality of ultrasound radiating members spaced along a distal region of the catheter. Each of the ultrasound radiating members has a resonant frequency at which ultrasonic energy is emitted with optimal effectiveness. The resonant frequency of an ultrasound radiating member is typically a fixed value based on the size, shape and material of the ultrasound radiating member. Because the resonant frequency of the ultrasound radiating member is fixed, a particular ultrasound radiating member can be used effectively only within a small range of frequencies.

Various applications of ultrasonic catheters, such as those discussed above, may apply ultrasonic energy at a different frequency in order to achieve the desired treatment. However, since a particular ultrasound radiating member has a fixed resonant frequency, that ultrasound radiating member is often useful for only a limited number of treatment applications. Therefore, conventional ultrasonic catheters must be constructed according to the particular application frequency.

Therefore, it is desired to provide an ultrasonic catheter capable of producing ultrasonic energy at multiple frequencies or across a wide range of frequencies, thus allowing a single catheter to be used in several different applications. One such ultrasonic catheter can be constructed by disposing a variety of different types of ultrasound radiating members along the catheter in a densely-packed relation. Preferably, such a catheter is capable of withstanding multiple ultrasound radiating member failures without producing excess thermal energy.

Such a catheter preferably has sufficiently small dimensions and sufficiently high flexibility such that it can be used in small vessels of the patient's anatomy. Such a catheter also preferably can be operated at relatively low power levels to prevent significant heat build-up at the treatment site. It is also desired to use a minimum number of parts in the manufacture of such an ultrasonic catheter for convenience and ease of manufacturing. In addition, to reduce production costs, it is also desired to provide an ultrasonic catheter having an inner core comprising a plurality of flat ultrasound elements mounted along a flat wire.

As such, according to one embodiment of the present invention, a catheter system for delivering ultrasonic energy and a therapeutic compound to a treatment site within a patient's vasculature comprises a tubular body. The tubular body has a proximal end, a distal end and an energy delivery section positioned between the proximal end and the distal end. The catheter system further comprises an inner core configured for insertion into the tubular body. The inner core has an outer surface and comprises an electrically conductive core material. The catheter system further comprises a plurality of ultrasound radiating members positioned on the outer surface of the inner core. The ultrasound radiating members are electrically connected to the electrically conductive core material. The catheter system further comprises an electrically conductive tube-shaped member disposed over the inner core and over the ultrasound radiating members positioned thereon. At least a portion of the electrically conductive tube-shaped member is electrically connected to a plurality of the ultrasound radiating members. The catheter system further comprises control circuitry configured to deliver an input signal to a plurality of the ultrasound radiating members.

According to another embodiment of the present invention, an ultrasonic catheter comprises an elongate tubular body having a hollow central lumen, a proximal end and a distal end. The ultrasonic catheter further comprises an inner core configured for insertion into the hollow central lumen. The inner core comprises a common wire and a plurality of ultrasound radiating members. The plurality of ultrasound radiating members are mounted on the common wire, and at least two of the ultrasound radiating members have a different resonant frequency.

According to another embodiment of the present invention, a method comprises positioning an ultrasonic catheter at a treatment site within a patient's vasculature. The ultrasonic catheter has an elongate inner core with a plurality of ultrasound radiating members disposed thereon. The ultrasound radiating members have a plurality of resonant frequencies. The method further comprises delivering a multi-frequency driving signal to the plurality of ultrasound radiating members. The frequencies comprising the multi-frequency driving signal include at least one of the resonant frequencies.

For purposes of summarizing the invention and the advantages achieved over the prior art, certain objects and advantages of the invention have been described above. It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment or embodiments disclosed.

BRIEF DESCRIPTION OF THE DRAWINGS

FIG. 7B is a cross-sectional view of the ultrasound assembly of FIG. 7A taken along line 7B—7B.

FIG. 7C is a cross-sectional view of the ultrasound assembly of FIG. 7A taken along line 7C—7C.

FIG. 11C is a cross-sectional view of the distal end of the ultrasonic catheter of FIG. 11B positioned at the treatment site before a treatment.

DETAILED DESCRIPTION OF PREFERRED EMBODIMENTS

Figure 1:
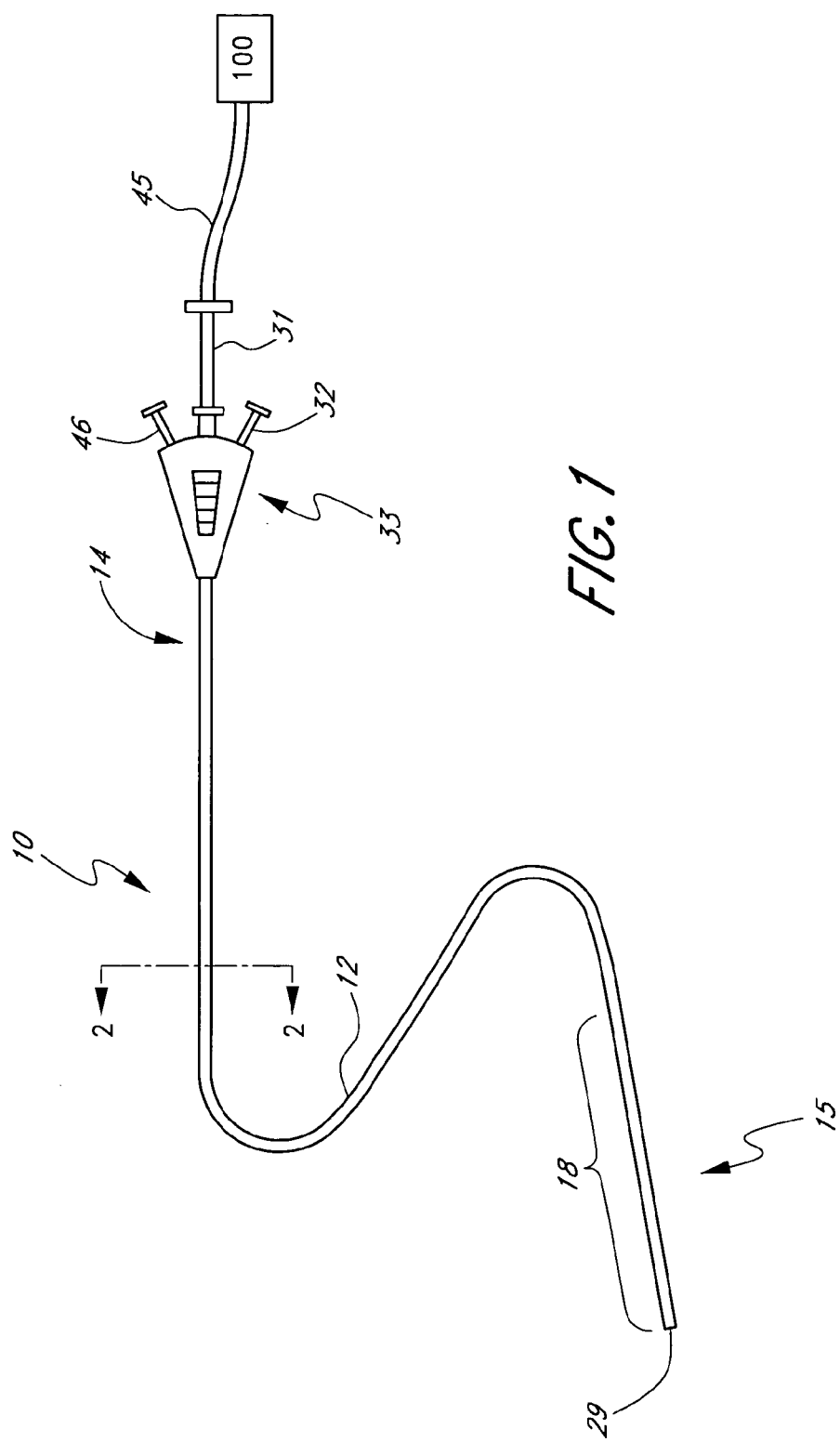
FIG. 1 is a schematic illustration of an ultrasonic catheter configured for insertion into large vessels of the human body.

As described above, it is desired to provide an ultrasonic catheter having various features and advantages. Examples of such features and advantages include the ability to deliver multi-frequency ultrasonic energy to a treatment site within a patient's vasculature. Preferred embodiments of an ultrasonic catheter having certain of these features and advantages are described herein. Methods of using such an ultrasonic catheter are also described herein.

The ultrasonic catheters described herein can be used to enhance the therapeutic effects of therapeutic compounds at a treatment site within a patient's body. As used herein, the term "therapeutic compound" refers broadly, without limitation, to a drug, medicament, dissolution compound, genetic material or any other substance capable of effecting physiological functions. Additionally, any mixture comprising any such substances is encompassed within this definition of "therapeutic compound", as well as any substance falling within the ordinary meaning of these terms. The enhancement of the effects of therapeutic compounds using ultrasonic energy is described in U.S. Pat. Nos. 5,318,014, 5,362,309, 5,474,531, 5,628,728, 6,001,069 and 6,210,356, the entire disclosure of which are hereby incorporated by herein by reference. Specifically, for applications that treat human blood vessels that have become partially or completely occluded by plaque, thrombi, emboli or other substances that reduce the blood carrying capacity of a vessel, suitable therapeutic compounds include, but are not limited to, an aqueous solution containing Heparin, Uronkinase, Streptokinase, TPA and BB-10153 (manufactured by British Biotech, Oxford, UK).

Certain features and aspects of the ultrasonic catheters disclosed herein may also find utility in applications where the ultrasonic energy itself provides a therapeutic effect. Examples of such therapeutic effects include preventing or reducing stenosis and/or restenosis; tissue ablation, abrasion or disruption; promoting temporary or permanent physiological changes in intracellular or intercellular structures; and rupturing micro-balloons or micro-bubbles for therapeutic compound delivery. Further information about such methods can be found in U.S. Pat. Nos. 5,261,291 and 5,431,663, the entire disclosure of which are hereby incorporated by herein by reference. Further information about using cavitation to produce biological effects can be found in U.S. Pat. No. RE36,939.

The ultrasonic catheters described herein are configured for applying ultrasonic energy over a substantial length of a body lumen, such as, for example, the larger vessels located in the leg. However, it should be appreciated that certain features and aspects of the present invention may be applied to catheters configured to be inserted into the small cerebral vessels, in solid tissues, in duct systems and in body cavities. Such catheters are described in U.S. patent application, entitled "Small Vessel Ultrasound Catheter" and filed Dec. 3, 2002. Additional embodiments that may be combined with certain features and aspects of the embodiments described herein are described in U.S. patent application, entitled "Ultrasound Assembly For Use With A Catheter" and filed Nov. 7, 2002, the entire disclosure of which is hereby incorporated herein by reference.

For purposes of summarizing the invention and the advantages achieved over the prior art, certain objects and advantages of the invention have been described above. It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

Ultrasound Catheter Structure and Use

With initial reference to FIG. 1, an ultrasonic catheter 10 configured for use in the large vessels of a patient's anatomy is schematically illustrated. For example, the ultrasonic catheter 10 illustrated in FIG. 1 can be used to treat long segment peripheral arterial occlusions, such as those in the vascular system of the leg.

As illustrated in FIG. 1, the ultrasonic catheter 10 generally comprises a multicomponent, elongate flexible tubular body 12 having a proximal region 14 and a distal region 15. The tubular body 12 includes a flexible energy delivery section 18 and a distal exit port 29 located in the distal region 15 of the catheter 10. A backend hub 33 is attached to the proximal region 14 of the tubular body 12, the backend hub 33 comprising a proximal access port 31, an inlet port 32 and a cooling fluid fitting 46. The proximal access port 31 can be connected to control circuitry 100 via cable 45.

The tubular body 12 and other components of the catheter 10 can be manufactured in accordance with any of a variety of techniques well known in the catheter manufacturing field. Suitable materials and dimensions can be readily selected based on the natural and anatomical dimensions of the treatment site and on the desired percutaneous access site.

For example, in a preferred embodiment the proximal region 14 of the tubular body 12 comprises a material that has sufficient flexibility, kink resistance, rigidity and structural support to push the energy delivery section 18 through the patient's vasculature to a treatment site. Examples of such materials include, but are not limited to, extruded polytetrafluoroethylene ("PTFE"), polyethylenes ("PE"), polyamides and other similar materials. In certain embodiments, the proximal region 14 of the tubular body 12 is reinforced by braiding, mesh or other constructions to provide increased kink resistance and pushability. For example, nickel titanium or stainless steel wires can be placed along or incorporated into the tubular body 12 to reduce kinking.

In an embodiment configured for treating thrombus in the arteries of the leg, the tubular body 12 has an outside diameter between about 0.060 inches and about 0.075 inches. In another embodiment, the tubular body 12 has an outside diameter of about 0.071 inches. In certain embodiments, the tubular body 12 has an axial length of approximately 105 centimeters, although other lengths may by appropriate for other applications.

The energy delivery section 18 of the tubular body 12 preferably comprises a material that is thinner than the material comprising the proximal region 14 of the tubular body 12 or a material that has a greater acoustic transparency. Thinner materials generally have greater acoustic transparency than thicker materials. Suitable materials for the energy delivery section 18 include, but are not limited to, high or low density polyethylenes, urethanes, nylons, and the like. In certain modified embodiments, the energy delivery section 18 may be formed from the same material or a material of the same thickness as the proximal region 14.

In certain embodiments, the tubular body 12 is divided into at least three sections of varying stiffness. The first section, which preferably includes the proximal region 14, has a relatively higher stiffness. The second section, which is located in an intermediate region between the proximal region 14 and the distal region 15 of the tubular body 12, has a relatively lower stiffness. This configuration further facilitates movement and placement of the catheter 10. The third section, which preferably includes the energy delivery section 18, generally has a lower stiffness than the second section.

Figure 2:
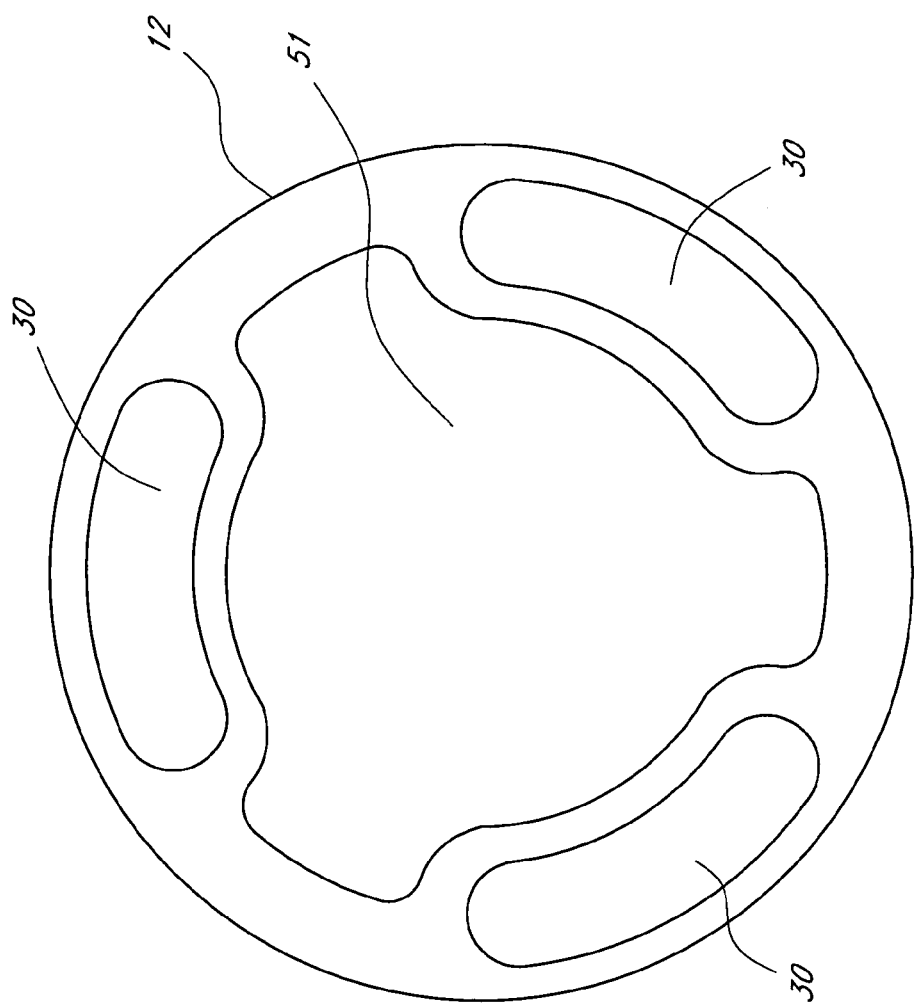
FIG. 2 is a cross-sectional view of the ultrasonic catheter of FIG. 1 taken along line 2—2.

FIG. 2 illustrates a cross section of the tubular body 12 taken along line 2—2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. The arrangement of the fluid delivery lumens 30 preferably provides a hollow central lumen 51 passing through the tubular body 12. The cross-section of the tubular body 12, as illustrated in FIG. 2, is preferably substantially constant along the length of the catheter 10. Thus, in such embodiments, substantially the same cross-section is present in both the proximal region 14 and the distal region 15 of the catheter 10, including the energy delivery section 18.

In certain embodiments, the central lumen 51 has a minimum diameter greater than about 0.030 inches. In another embodiment, the central lumen 51 has a minimum diameter greater than about 0.037 inches. In one preferred embodiment, the fluid delivery lumens 30 have dimensions of about 0.026 inches wide by about 0.0075 inches high, although other dimensions may be used in other applications.

As described above, the central lumen 51 preferably extends through the length of the tubular body 12. As illustrated in FIG. 1, the central lumen 51 preferably has a distal exit port 29 and a proximal access port 31. The proximal access port 31 forms part of the backend hub 33, which is attached to the proximal region 14 of the catheter 10. The backend hub 33 preferably further comprises cooling fluid fitting 46, which is hydraulically connected to the central lumen 51. The backend hub 33 also preferably comprises a therapeutic compound inlet port 32, which is in hydraulic connection with the fluid delivery lumens 30, and which can be hydraulically coupled to a source of therapeutic compound via a hub such as a Luer fitting.

Figure 3:
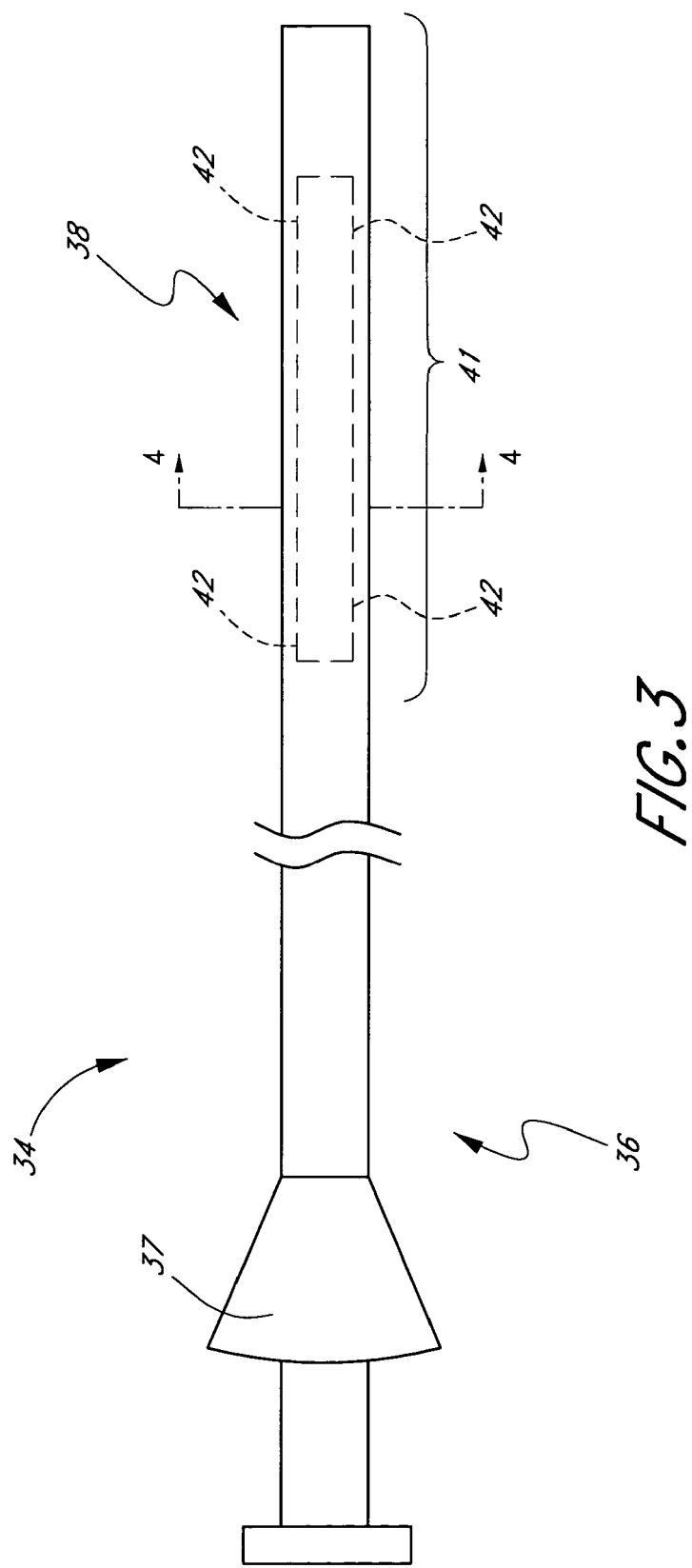
FIG. 3 is a schematic illustration of an elongate inner core configured to be positioned within the central lumen of the catheter illustrated in FIG. 2.

The central lumen 51 is configured to receive an elongate inner core 34 of which a preferred embodiment is illustrated in FIG. 3. The elongate inner core 34 preferably comprises a proximal region 36 and a distal region 38. Proximal hub 37 is fitted on the inner core 34 at one end of the proximal region 36. One or more ultrasound radiating members are positioned within an inner core energy delivery section 41 located within the distal region 38. The ultrasound radiating members form an ultrasound assembly 42, which will be described in greater detail below.

Figure 4:
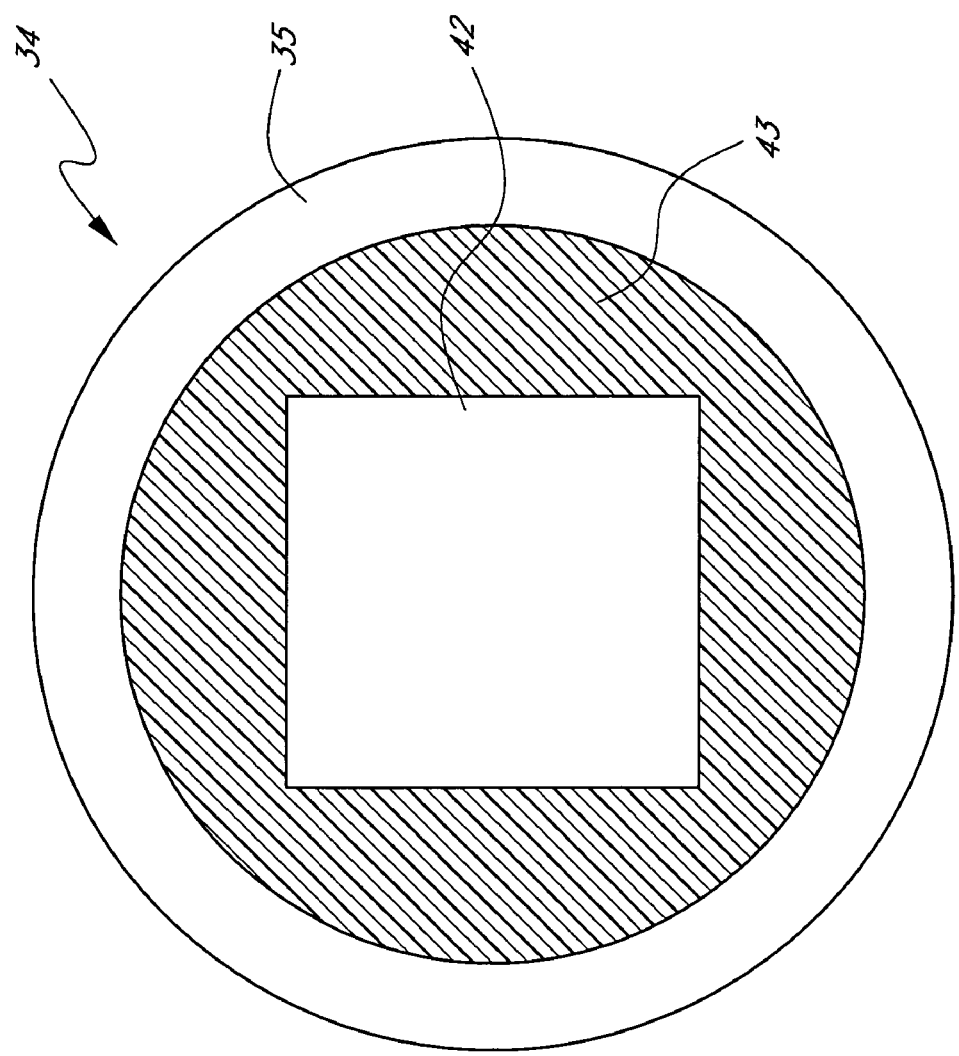
FIG. 4 is a cross-sectional view of the elongate inner core of FIG. 3 taken along line 4—4.

As shown in the cross-section illustrated in FIG. 4, which is taken along lines 4—4 in FIG. 3, the inner core 34 preferably has a cylindrical shape, with an outer diameter that permits the inner core 34 to be inserted into the central lumen 51 of the tubular body 12 via the proximal access port 31. Suitable outer diameters of the inner core 34 include, but are not limited to, about 0.010 inches to about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, the inner core 34 preferably comprises a cylindrical outer body 35 that houses the ultrasound assembly 42. The ultrasound assembly 42 comprises wiring and ultrasound radiating members, described in greater detail in FIGS. 5 through 7D, such that the ultrasound assembly 42 is capable of radiating ultrasonic energy from the energy delivery section 41 of the inner core 34. The ultrasound assembly 42 is electrically connected to the backend hub 33, where the inner core 34 can be connected to control circuitry 100 via cable 45 (illustrated in FIG. 1). Preferably, an electrically insulating potting material 43 fills the inner core 34, surrounding the ultrasound assembly 42, thus preventing movement of the ultrasound assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
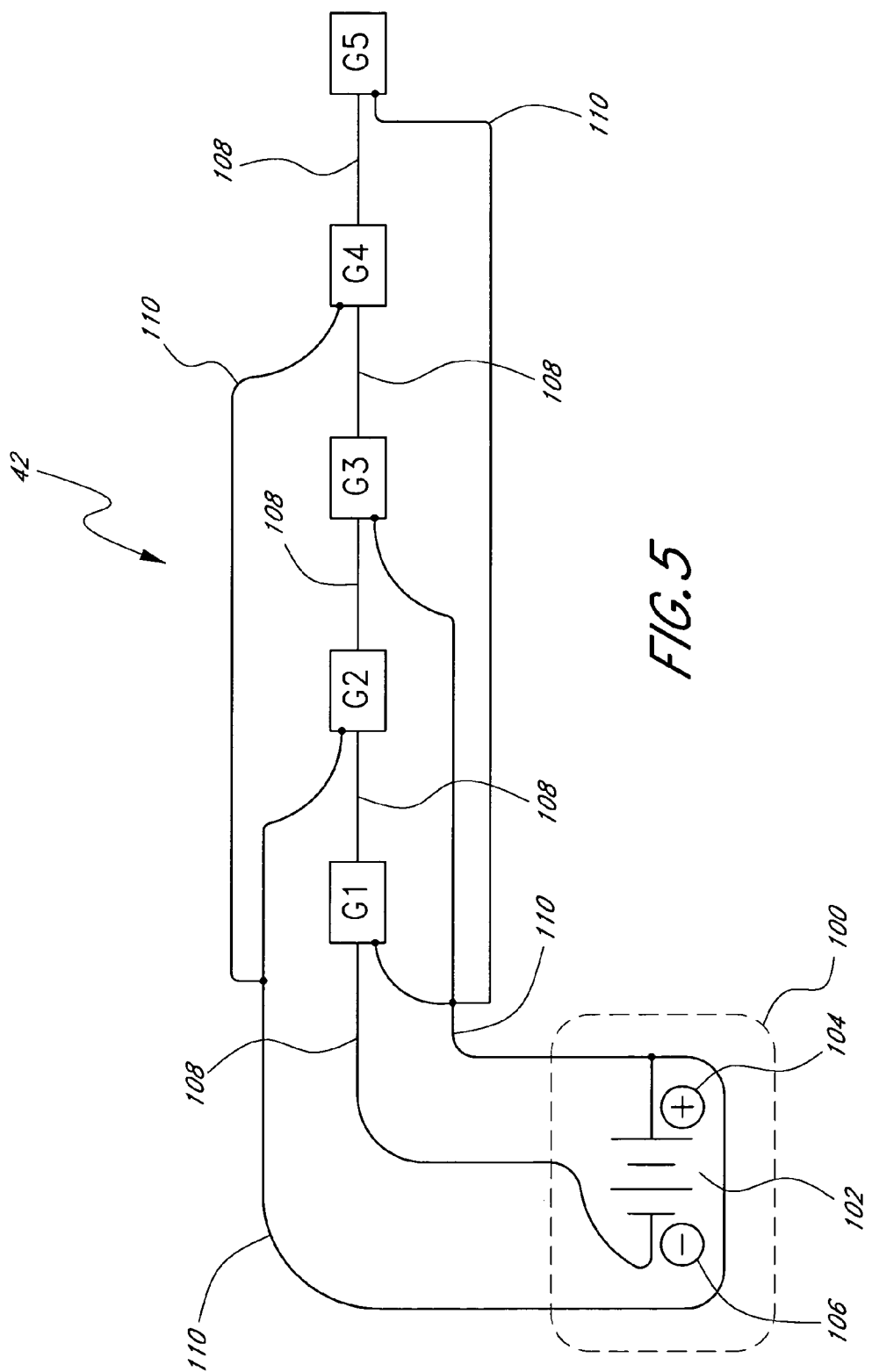
FIG. 5 is a schematic wiring diagram illustrating a preferred technique for electrically connecting five groups of ultrasound radiating members to form an ultrasound assembly.
Figure 6:
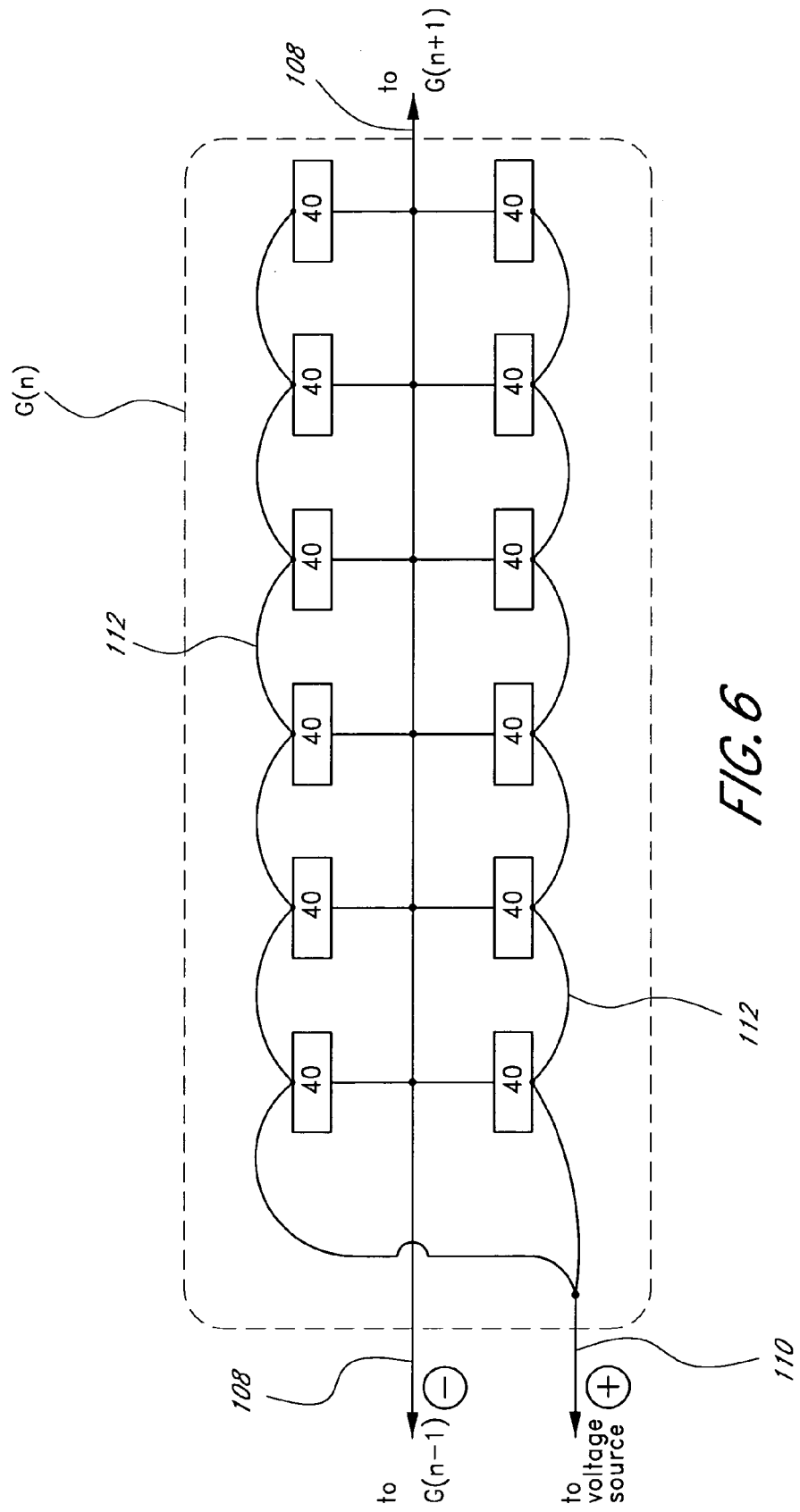
FIG. 6 is a schematic wiring diagram illustrating a preferred technique for electrically connecting one of the groups of FIG. 5.

In a preferred embodiment, the ultrasound assembly 42 comprises a plurality of ultrasound radiating members that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 comprises five groups G1, G2, G3, G4, G5 of ultrasound radiating members 40 that are electrically connected to each other. The five groups are also electrically connected to the control circuitry 100.

As used herein, the terms "ultrasonic energy", "ultrasound" and "ultrasonic" are broad terms, having their ordinary meanings, and further refer to, without limitation, mechanical energy transferred through longitudinal pressure or compression waves. Ultrasonic energy can be emitted as continuous or pulsed waves, depending on the requirements of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy has a frequency between about 20 kHz and about 20 MHz. For example, in one embodiment, the waves have a frequency between about 500 kHz and about 20 MHz. In another embodiment, the waves have a frequency between about 1 MHz and about 3 MHz. In yet another embodiment, the waves have a frequency of about 2 MHz. The average acoustic power is between about 0.01 watts and 300 watts. In one embodiment, the average acoustic power is about 15 watts.

As used herein, the term "ultrasound radiating member" refers to any apparatus capable of producing ultrasonic energy. For example, in one embodiment, an ultrasound radiating member comprises an ultrasonic transducer, which converts electrical energy into ultrasonic energy. A suitable example of an ultrasonic transducer for generating ultrasonic energy from electrical energy includes, but is not limited to, piezoelectric ceramic oscillators. Piezoelectric ceramics typically comprise a crystalline material, such as quartz, that change shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member.

Still referring to FIG. 5, the control circuitry 100 preferably comprises, among other things, a voltage source 102. The voltage source 102 comprises a positive terminal 104 and a negative terminal 106. The negative terminal 106 is connected to common wire 108, which connects the five groups G1–G5 of ultrasound radiating members 40 in series. The positive terminal 104 is connected to a plurality of lead wires 110, which each connect to one of the five groups G1–G5 of ultrasound radiating members 40. Thus, under this configuration, each of the five groups G1–G5, one of which is illustrated in FIG. 6, is connected to the positive terminal 104 via one of the lead wires 110, and to the negative terminal 106 via the common wire 108.

Referring now to FIG. 6, each group G1–G5 comprises a plurality of ultrasound radiating members 40. Each of the ultrasound radiating members 40 is electrically connected to the common wire 108 and to the lead wire 110 via one of two positive contact wires 112. Thus, when wired as illustrated, a constant voltage difference will be applied to each ultrasound radiating member 40 in the group. Although the group illustrated in FIG. 6 comprises twelve ultrasound radiating members 40, one of ordinary skill in the art will recognize that more or fewer ultrasound radiating members 40 can be included in the group. Likewise, more or fewer than five groups can be included within the ultrasound assembly 42 illustrated in FIG. 5.

Figure 7A:
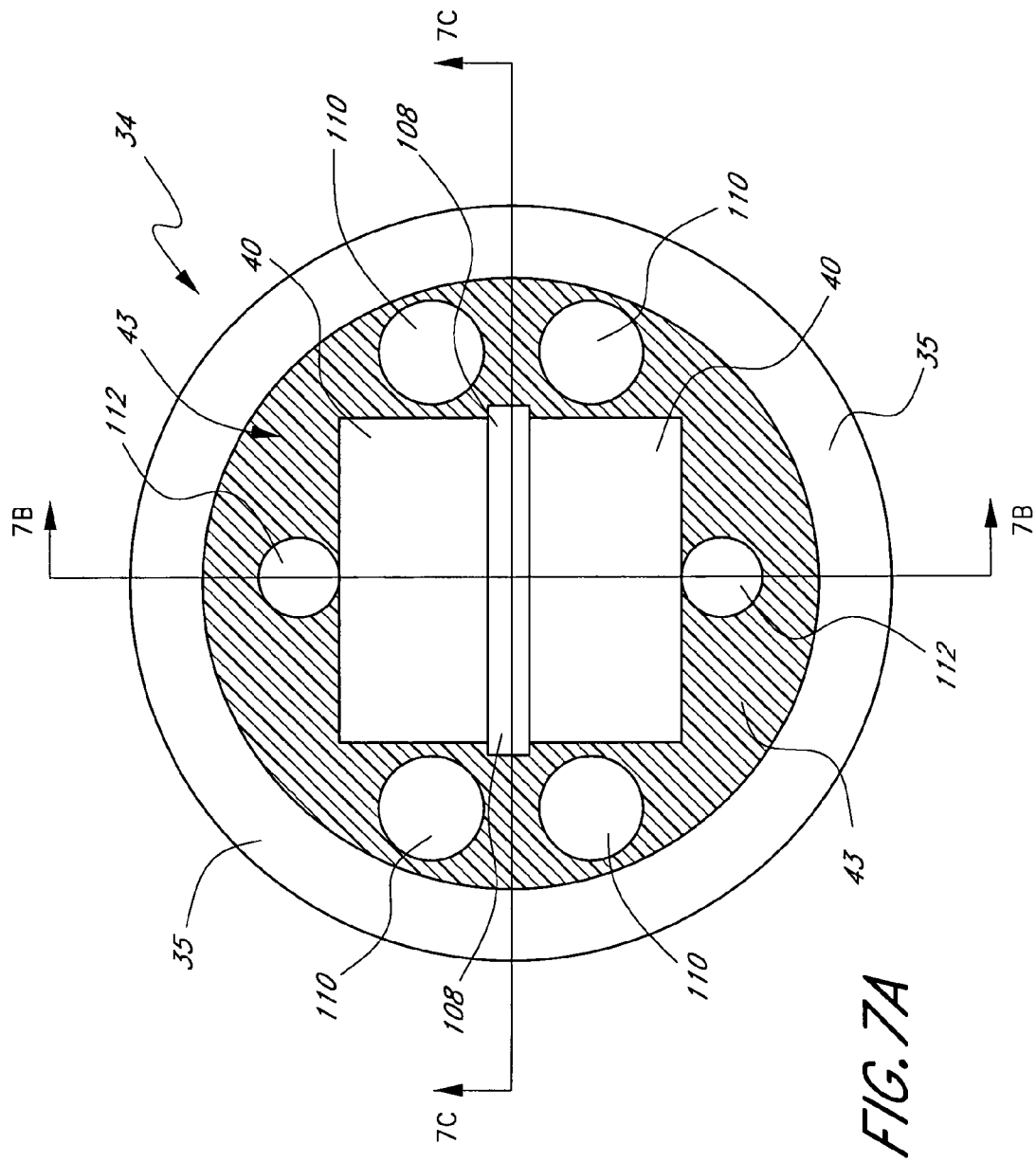
FIG. 7A is a schematic illustration of the ultrasound assembly of FIG. 5 housed within the inner core of FIG. 4.

FIG. 7A illustrates one preferred technique for arranging the components of the ultrasound assembly 42 (as schematically illustrated in FIG. 5) into the inner core 34 (as schematically illustrated in FIG. 4). FIG. 7A is a cross-sectional view of the ultrasound assembly 42 taken within group G1 in FIG. 5, as indicated by the presence of four lead wires 110. For example, if a cross-sectional view of the ultrasound assembly 42 was taken within group G4 in FIG. 5, only one lead wire 110 would be present (that is, the one lead wire connecting group G5).

Referring still to FIG. 7A, the common wire 108 comprises an elongate, flat piece of electrically conductive material in electrical contact with a pair of ultrasound radiating members 40. Each of the ultrasound radiating members 40 is also in electrical contact with a positive contact wire 112. Because the common wire 108 is connected to the negative terminal 106, and the positive contact wire 112 is connected to the positive terminal 104, a voltage difference can be created across each ultrasound radiating member 40. Lead wires 110 are preferably separated from the other components of the ultrasound assembly 42, thus preventing interference with the operation of the ultrasound radiating members 40 as described above. For example, in one preferred embodiment, the inner core 34 is filled with an insulating potting material 43, thus deterring unwanted electrical contact between the various components of the ultrasound assembly 42.

FIGS. 7B and 7C illustrate cross sectional views of the inner core 34 of FIG. 7A taken along lines 7B—7B and 7C—7C, respectively. As illustrated in FIG. 7B, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 7C, the common wire 108 preferably comprises wide regions 108W upon which the ultrasound radiating members 40 can be mounted, thus reducing the likelihood that the paired ultrasound radiating members 40 will short together. In certain embodiments, outside the wide regions 108W, the common wire 108 may have a more conventional, rounded wire shape.

Figure 7D:
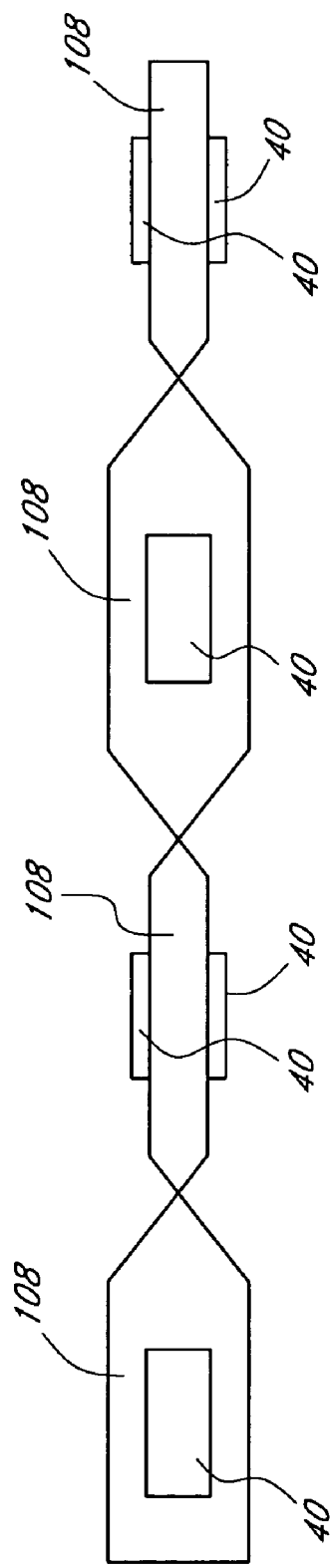
FIG. 7D is a side view of an ultrasound assembly center wire twisted into a helical configuration.

In a modified embodiment, such as illustrated in FIG. 7D, the common wire 108 is twisted to form a helical shape before being fixed within the inner core 34. In such embodiments, the ultrasound radiating members 40 are oriented in a plurality of radial directions, thus enhancing the radial uniformity of the resulting ultrasonic energy field.

One of ordinary skill in the art will recognize that the wiring arrangement described above can be modified to allow each group G1, G2, G3, G4, G5 to be independently powered. Specifically, by providing a separate power source within the control system 100 for each group, each group can be individually turned on or off, or can be driven with an individualized power. This provides the advantage of allowing the delivery of ultrasonic energy to be "turned off" in regions of the treatment site where treatment is complete, thus preventing deleterious or unnecessary ultrasonic energy to be applied to the patient.

The embodiments described above, and illustrated in FIGS. 5 through 7, illustrate a plurality of ultrasound radiating members grouped spatially. That is, in such embodiments, all of the ultrasound radiating members within a certain group are positioned adjacent to each other, such that when a single group is activated, ultrasonic energy is delivered at a specific length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the energy delivery section. Such modified embodiments may be advantageous in applications wherein it is desired to deliver a less focussed, more diffuse ultrasonic energy field to the treatment site.

In a preferred embodiment, the ultrasound radiating members 40 comprise rectangular lead zirconate titanate ("PZT") ultrasound transducers that have dimensions of about 0.017 inches by about 0.010 inches by about 0.080 inches. In other embodiments, other configurations may be used. For example, disc-shaped ultrasound radiating members 40 can be used in other embodiments. In a preferred embodiment, the common wire 108 comprises copper, and is about 0.005 inches thick, although other electrically conductive materials and other dimensions can be used in other embodiments. Lead wires 110 are preferably 36-gauge electrical conductors, while positive contact wires 112 are preferably 42-gauge electrical conductors. However, one of ordinary skill in the art will recognize that other wire gauges can be used in other embodiments.

As described above, suitable frequencies for the ultrasound radiating member 40 include, but are not limited to, from about 20 kHz to about 20 MHz. In one embodiment, the frequency is between about 500 kHz and 20 MHz, and in another embodiment the frequency is between about 1 MHz and 3 MHz. In yet another embodiment, the ultrasound radiating members 40 are operated with a frequency of about 2 MHz.

Figure 8:
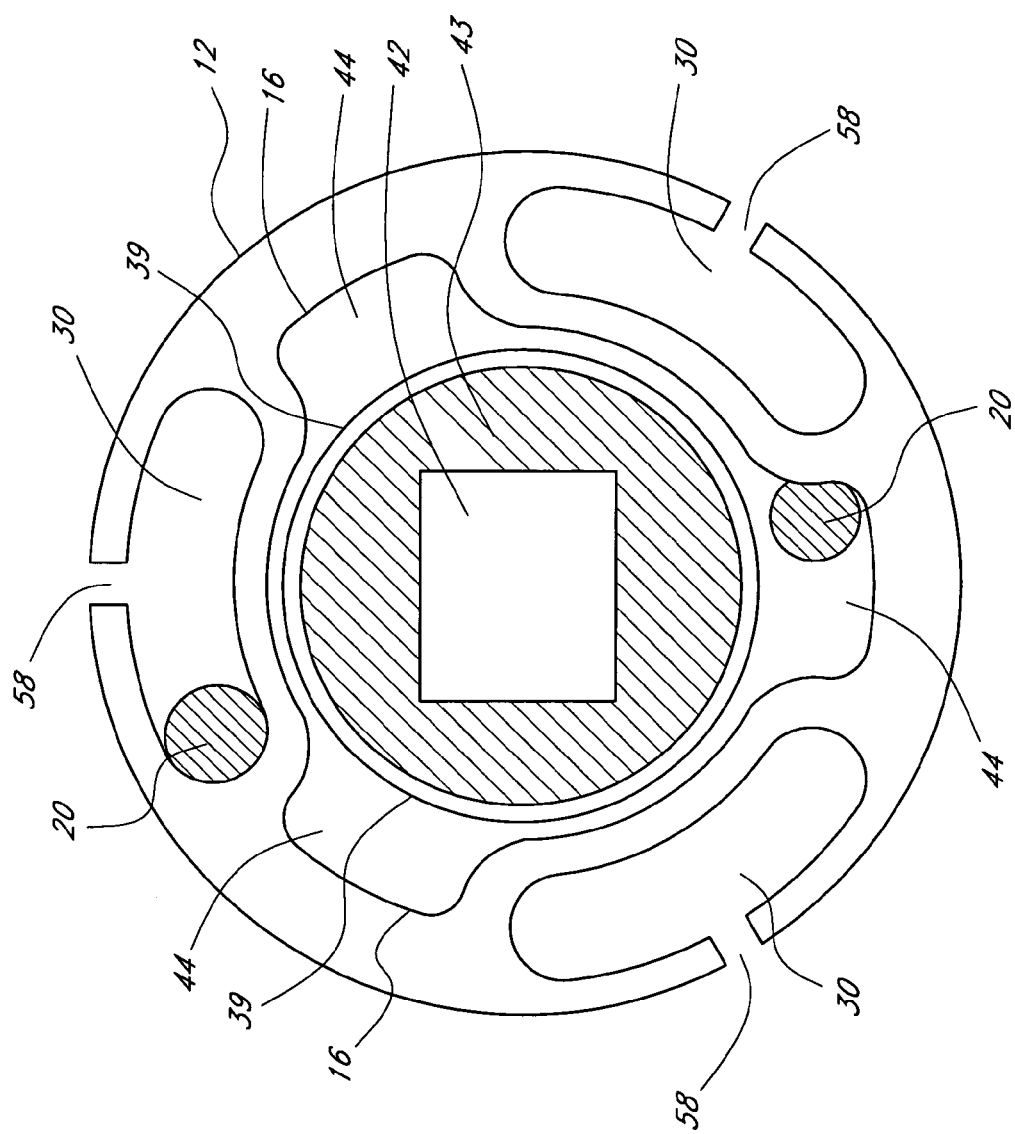
FIG. 8 illustrates the energy delivery section of the inner core of FIG. 4 positioned within the energy delivery section of the tubular body of FIG. 2.

FIG. 8 illustrates the inner core 34 positioned within the tubular body 12. Details of the ultrasound assembly 42, provided in FIG. 7A, are omitted for clarity. As described above, the inner core 34 can be slid within the central lumen 51 of the tubular body 12, thereby allowing the inner core energy delivery section 41 to be positioned within the tubular body energy delivery section 18. For example, in a preferred embodiment, the materials comprising the inner core energy delivery section 41, the tubular body energy delivery section 18, and the potting material 43 all comprise materials having a similar acoustic impedance, thereby minimizing ultrasonic energy losses across material interfaces.

FIG. 8 further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. Thus, a source of therapeutic compound coupled to the inlet port 32 provides a hydraulic pressure which drives the therapeutic compound through the fluid delivery lumens 30 and out the fluid delivery ports 58.

By evenly spacing the fluid delivery lumens 30 around the circumference of the tubular body 12, as illustrated in FIG.

8, a substantially even flow of therapeutic compound around the circumference of the tubular body 12 can be achieved. In addition, the size, location and geometry of the fluid delivery ports 58 can be selected to provide uniform fluid flow from the fluid delivery lumen 30 to the treatment site. For example, in one embodiment, fluid delivery ports 58 closer to the proximal region of the energy delivery section 18 have smaller diameters than fluid delivery ports 58 closer to the distal region of the energy delivery section 18, thereby allowing uniform delivery of fluid across the entire energy delivery section 18.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to 0.0020 inches in the distal region of the energy delivery section 18. The increase in size between adjacent fluid delivery ports 58 depends on the material comprising the tubular body 12, and on the size of the fluid delivery lumen 30. The fluid delivery ports 58 can be created in the tubular body 12 by punching, drilling, burning or ablating (such as with a laser), or by any other suitable method. Therapeutic compound flow along the length of the tubular body 12 can also be increased by increasing the density of the fluid delivery ports 58 toward the distal region 15 of the tubular body 12.

It should be appreciated that it may be desirable to provide non-uniform fluid flow from the fluid delivery ports 58 to the treatment site. In such embodiment, the size, location and geometry of the fluid delivery ports 58 can be selected to provide such non-uniform fluid flow.

Referring still to FIG. 8, placement of the inner core 34 within the tubular body 12 further defines cooling fluid lumens 44. Cooling fluid lumens 44 are formed between an outer surface 39 of the inner core 34 and an inner surface 16 of the tubular body 12. In certain embodiments, a cooling fluid is introduced through the proximal access port 31 such that cooling fluid flow is produced through cooling fluid lumens 44 and out distal exit port 29 (see FIG. 1). The cooling fluid lumens 44 are preferably evenly spaced around the circumference of the tubular body 12 (that is, at approximately 120° increments for a three-lumen configuration), thereby providing uniform cooling fluid flow over the inner core 34. Such a configuration is desired to remove unwanted thermal energy at the treatment site. As will be explained below, the flow rate of the cooling fluid and the power to the ultrasound assembly 42 can be adjusted to maintain the temperature of the inner core energy delivery section 41 within a desired range.

In a preferred embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, the inner core outer body 35 preferably comprises a material having the ability to transmit torque. Suitable materials for the inner core outer body 35 include, but are not limited to, polyimides, polyesters, polyurethanes, thermoplastic elastomers and braided polyimides.

In a preferred embodiment, the fluid delivery lumens 30 and the cooling fluid lumens 44 are open at the distal end of the tubular body 12, thereby allowing the therapeutic compound and the cooling fluid to pass into the patient's vasculature at the distal exit port. Or, if desired, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can prevented from passing through the distal exit port by configuring the inner core 34 to have a length that is less than the length of the tubular body 12. In other embodiments, a protrusion is formed on the inner surface 16 of the tubular body 12 in the distal region 15, thereby preventing the inner core 34 from passing through the distal exit port 29.

In still other embodiments, the catheter 10 further comprises an occlusion device (not shown) positioned at the distal exit port 29. The occlusion device preferably has a reduced inner diameter that can accommodate a guidewire, but that is less than the outer diameter of the central lumen 51. Thus, the inner core 34 is prevented from extending through the occlusion device and out the distal exit port 29. For example, suitable inner diameters for the occlusion device include, but are not limited to, about 0.005 inches to about 0.050 inches. In other embodiments, the occlusion device has a closed end, thus preventing cooling fluid from leaving the catheter 10, and instead recirculating to the proximal region 14 of the tubular body 12. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In certain embodiments, as illustrated in FIG. 8, the tubular body 12 further comprises one or more temperature sensors 20, which are preferably located within the energy delivery section 18. In such embodiments, the proximal region 14 of the tubular body 12 includes a temperature sensor lead wire (not shown) which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30, and/or within one or more of the cooling fluid lumens 44.

Figure 9:
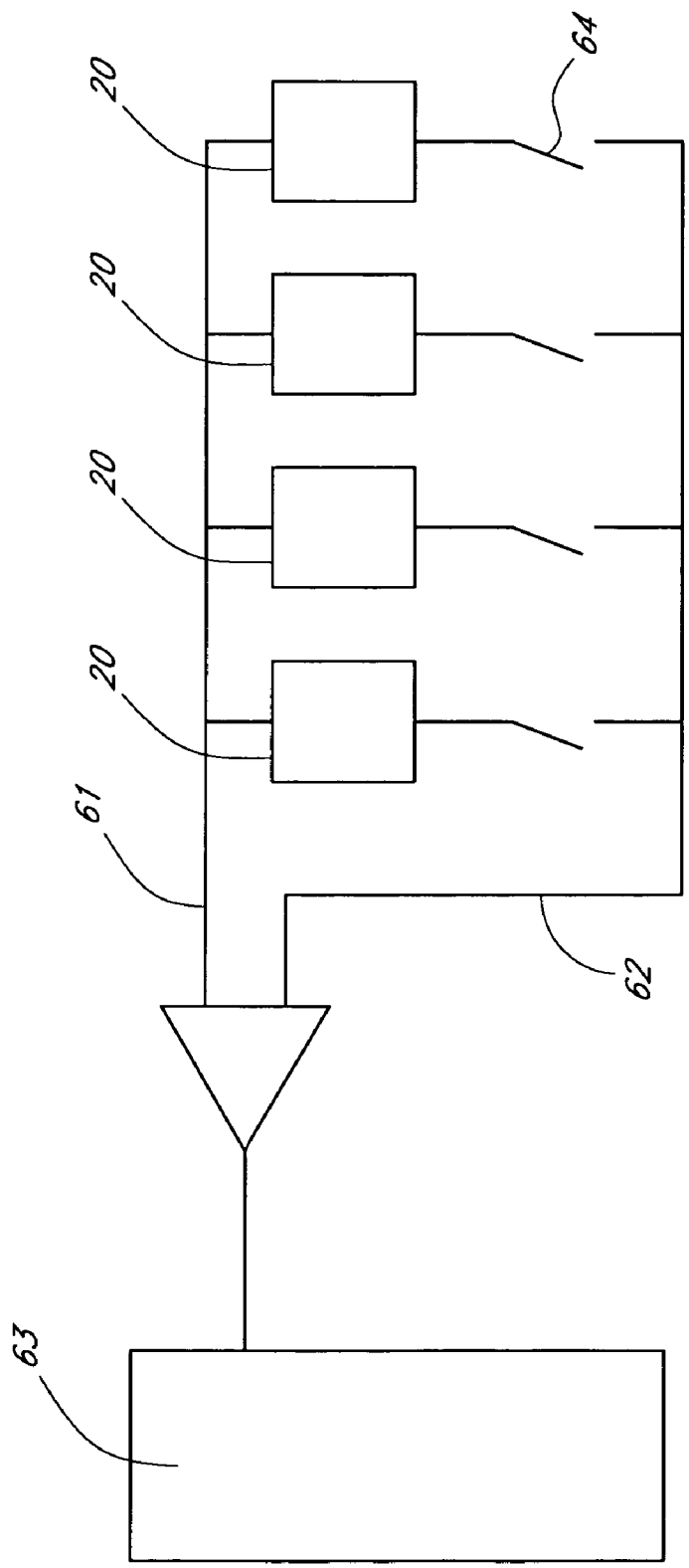
FIG. 9 illustrates a wiring diagram for connecting a plurality of temperature sensors with a common wire.

FIG. 9 illustrates one embodiment for electrically connecting the temperature sensors 20. In such embodiments, each temperature sensor 20 is coupled to a common wire 61 and is associated with an individual return wire 62. Accordingly, n+1 wires can be used to independently sense the temperature at n distinct temperature sensors 20. The temperature at a particular temperature sensor 20 can be determined by closing a switch 64 to complete a circuit between that thermocouple's individual return wire 62 and the common wire 61. In embodiments wherein the temperature sensors 20 comprise thermocouples, the temperature can be calculated from the voltage in the circuit using, for example, a sensing circuit 63, which can be located within the external control circuitry 100.

In other embodiments, each temperature sensor 20 is independently wired. In such embodiments, 2n wires pass through the tubular body 12 to independently sense the temperature at n independent temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Figure 10:
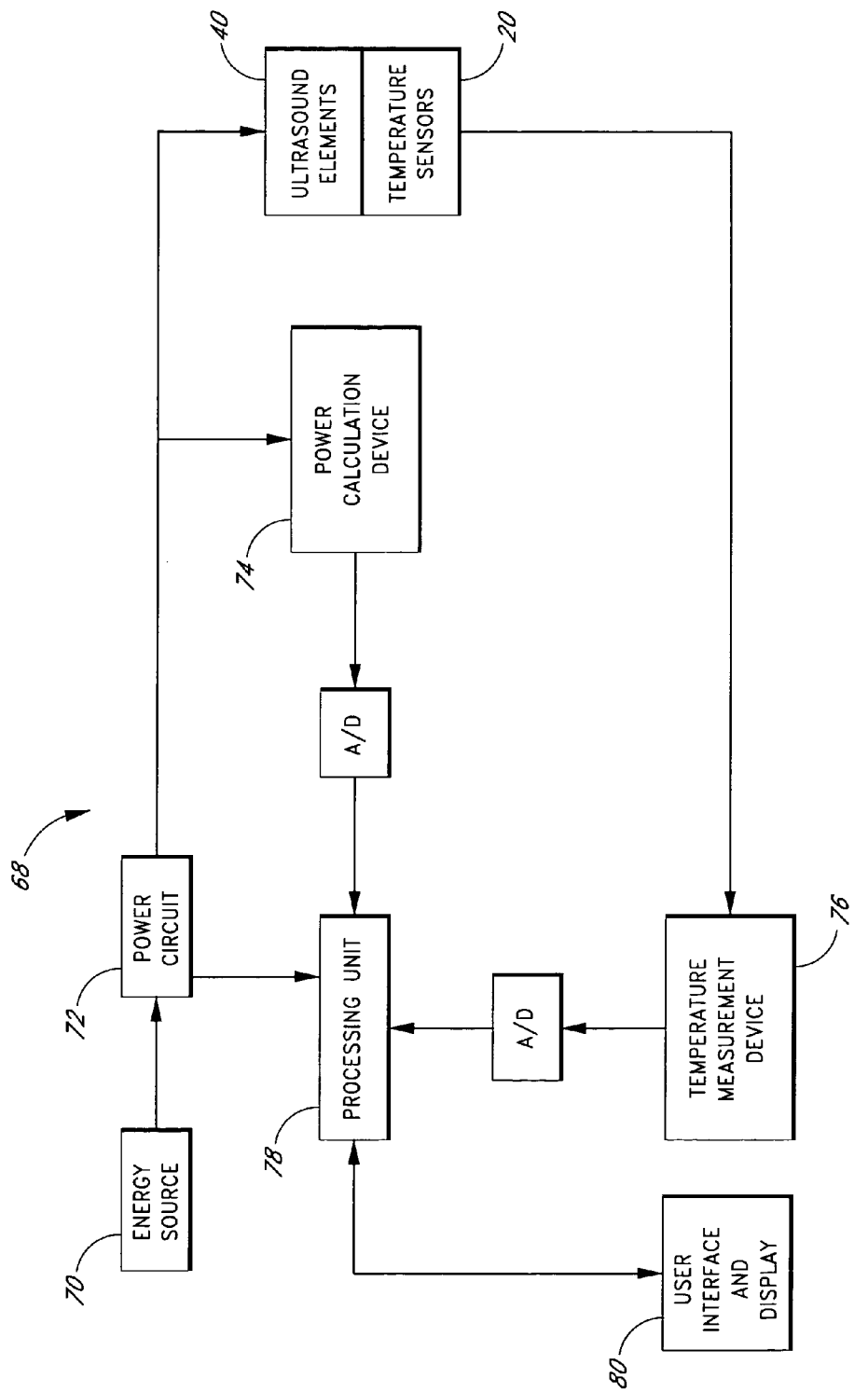
FIG. 10 is a block diagram of a feedback control system for use with an ultrasonic catheter.

FIG. 10 illustrates one embodiment of a feedback control system 68 that can be used with the catheter 10. The feedback control system 68 can be integrated into the control system that is connected to the inner core 34 via cable 45 (as illustrated in FIG. 1). The feedback control system 68 allows the temperature at each temperature sensor 20 to be monitored and allows the output power of the energy source 70 to be adjusted accordingly. A physician can, if desired, override the closed or open loop system.

The feedback control system 68 preferably comprises an energy source 70, power circuits 72 and a power calculation device 74 that is coupled to the ultrasound radiating members 40. A temperature measurement device 76 is coupled to the temperature sensors 20 in the tubular body 12. A processing unit 78 is coupled to the power calculation device 74, the power circuits 72 and a user interface and display 80.

In operation, the temperature at each temperature sensor 20 is determined by the temperature measurement device 76. The processing unit 78 receives each determined temperature from the temperature measurement device 76. The determined temperature can then be displayed to the user at the user interface and display 80.

The processing unit 78 comprises logic for generating a temperature control signal. The temperature control signal is proportional to the difference between the measured temperature and a desired temperature. The desired temperature can be determined by the user (set at the user interface and display 80) or can be preset within the processing unit 78.

The temperature control signal is received by the power circuits 72. The power circuits 72 are preferably configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 is preferably reduced in response to that temperature control signal. Similarly, when the temperature control signal is below a particular level, the power supplied to a particular group of ultrasound radiating members 40 is preferably increased in response to that temperature control signal. After each power adjustment, the processing unit 78 preferably monitors the temperature sensors 20 and produces another temperature control signal which is received by the power circuits 72.

The processing unit 78 preferably further comprises safety control logic. The safety control logic detects when the temperature at a temperature sensor 20 has exceeded a safety threshold. The processing unit 78 can then provide a temperature control signal which causes the power circuits 72 to stop the delivery of energy from the energy source 70 to that particular group of ultrasound radiating members 40.

Because, in certain embodiments, the ultrasound radiating members 40 are mobile relative to the temperature sensors 20, it can be unclear which group of ultrasound radiating members 40 should have a power, voltage, phase and/or current level adjustment. Consequently, each group of ultrasound radiating member 40 can be identically adjusted in certain embodiments. In a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 also receives a power signal from a power calculation device 74. The power signal can be used to determine the power being received by each group of ultrasound radiating members 40. The determined power can then be displayed to the user on the user interface and display 80.

As described above, the feedback control system 68 can be configured to maintain tissue adjacent to the energy delivery section 18 below a desired temperature. For example, it is generally desirable to prevent tissue at a treatment site from increasing more than 6° C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as for example a computer with software. When the processing unit 78 is a computer it can include a central processing unit ("CPU") coupled through a system bus. As is well known in the art, the user interface and display 80 can comprise a mouse, a keyboard, a disk drive, a display monitor, a nonvolatile memory system, or any another. Also preferably coupled to the bus is a program memory and a data memory.

In lieu of the series of power adjustments described above, a profile of the power to be delivered to each group of ultrasound radiating members 40 can be incorporated into the processing unit 78, such that a preset amount of ultrasonic energy to be delivered is pre-profiled. In such embodiments, the power delivered to each group of ultrasound radiating members 40 can then be adjusted according to the preset profiles.

The ultrasound radiating members 40 are preferably operated in a pulsed mode. For example, in one embodiment, the time average power supplied to the ultrasound radiating members 40 is preferably between about 0.1 watts and 2 watts and more preferably between about 0.5 watts and 1.5 watts. In certain preferred embodiments, the time average power is approximately 0.6 watts or 1.2 watts. The duty cycle is preferably between about 1% and 50% and more preferably between about 5% and 25%. In certain preferred embodiments, the duty ratio is approximately 7.5% or 15%. The pulse averaged power is preferably between about 0.1 watts and 20 watts and more preferably between approximately 5 watts and 20 watts. In certain preferred embodiments, the pulse averaged power is approximately 8 watts and 16 watts. The amplitude during each pulse can be constant or varied.

In one embodiment, the pulse repetition rate is preferably between about 5 Hz and 150 Hz and more preferably between about 10 Hz and 50 Hz. In certain preferred embodiments, the pulse repetition rate is approximately 30 Hz. The pulse duration is preferably between about 1 millisecond and 50 milliseconds and more preferably between about 1 millisecond and 25 milliseconds. In certain preferred embodiments, the pulse duration is approximately 2.5 milliseconds or 5 milliseconds.

In one particular embodiment, the ultrasound radiating members 40 are operated at an average power of approximately 0.6 watts, a duty cycle of approximately 7.5%, a pulse repetition rate of 30 Hz, a pulse average electrical power of approximately 8 watts and a pulse duration of approximately 2.5 milliseconds.

The ultrasound radiating members 40 used with the electrical parameters described herein preferably has an acoustic efficiency greater than 50% and more preferably greater than 75%. The ultrasound radiating members 40 can be formed a variety of shapes, such as, cylindrical (solid or hollow), flat, bar, triangular, and the like. The length of the ultrasound radiating members 40 is preferably between about 0.1 cm and about 0.5 cm. The thickness or diameter of the ultrasound radiating members 40 is preferably between about 0.02 cm and about 0.2 cm.

Figure 11A:
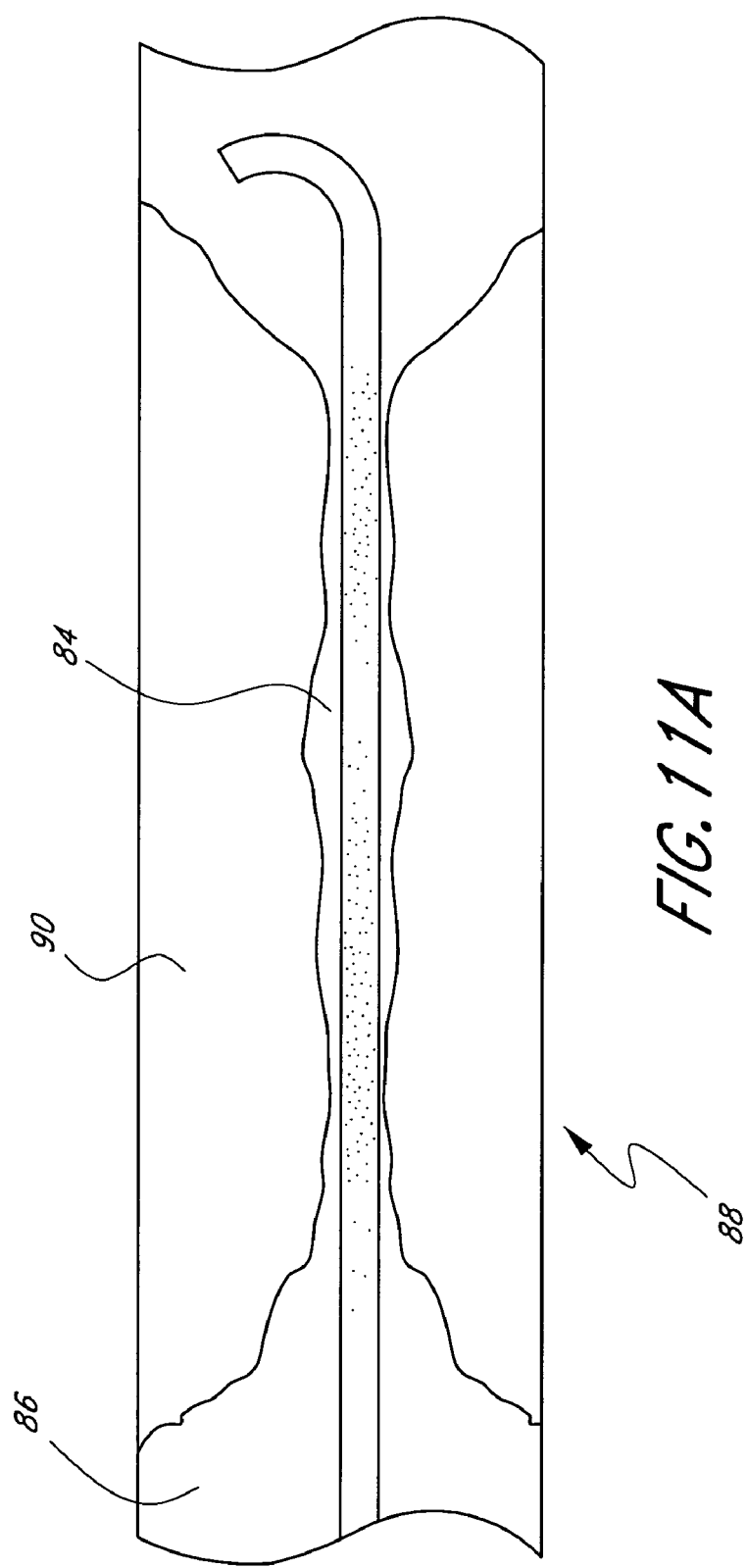
FIG. 11A is a side view of a treatment site.

FIGS. 11A through 11D illustrate a method for using the ultrasonic catheter 10. As illustrated in FIG. 11A, a guidewire 84 similar to a guidewire used in typical angioplasty procedures is directed through a patient's vessels 86 to a treatment site 88 which includes a clot 90. The guidewire 84 is directed through the clot 90. Suitable vessels 86 include, but are not limited to, the large periphery and the small cerebral blood vessels of the body. Additionally, as mentioned above, the ultrasonic catheter 10 also has utility in various imaging applications or in applications for treating and/or diagnosing other diseases in other body parts.

Figure 11B:
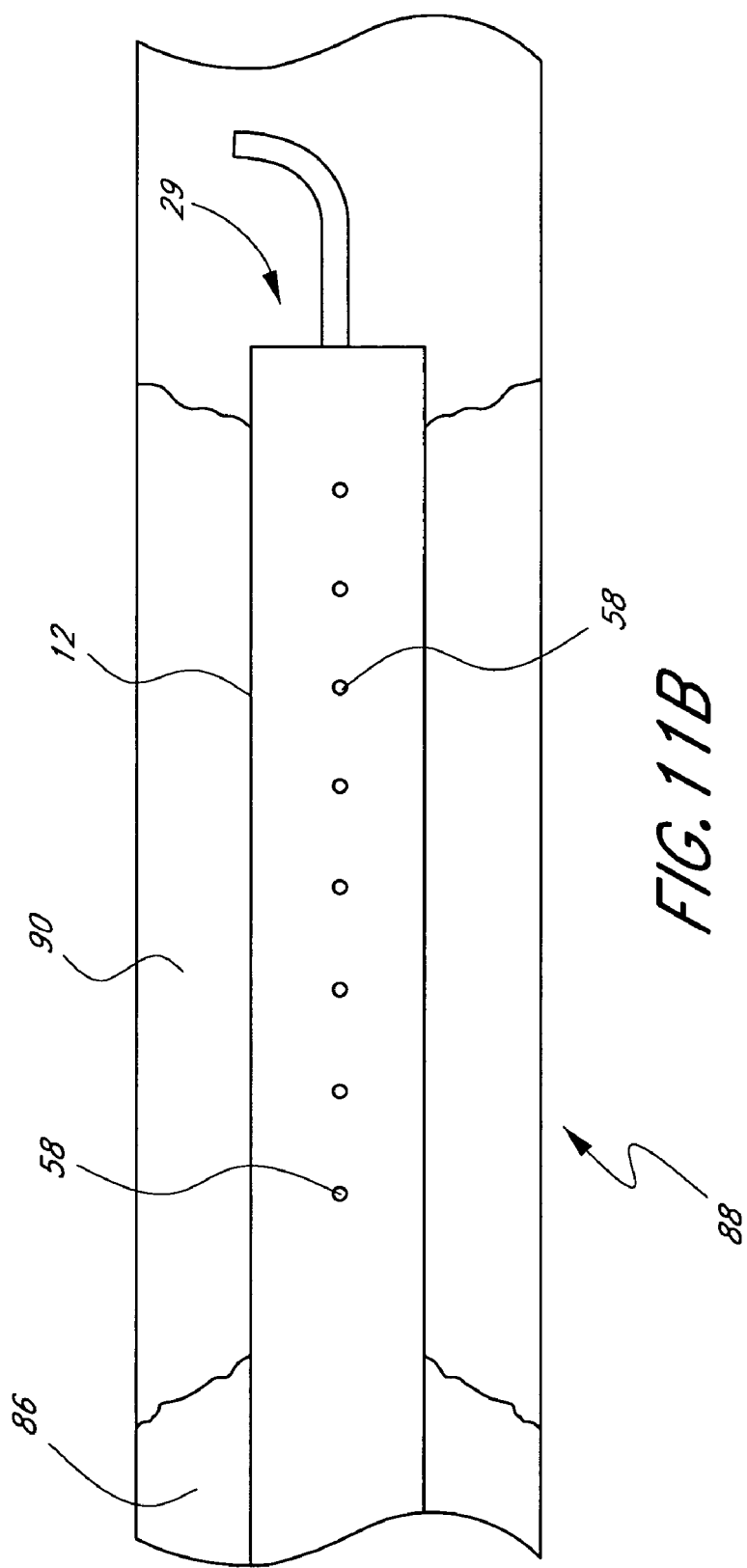
FIG. 11B is a side view of the distal end of an ultrasonic catheter positioned at the treatment site of FIG. 11A.

As illustrated in FIG. 11B, the tubular body 12 is slid over and is advanced along the guidewire 84 using conventional over-the-guidewire techniques. The tubular body 12 is advanced until the energy delivery section 18 of the tubular body 12 is positioned at the clot 90. In certain embodiments, radiopaque markers (not shown) are positioned along the energy delivery section 18 of the tubular body 12 to aid in the positioning of the tubular body 12 within the treatment site 88.

As illustrated in FIG. 11C, the guidewire 84 is then withdrawn from the tubular body 12 by pulling the guidewire 84 from the proximal region 14 of the catheter 10 while holding the tubular body 12 stationary. This leaves the tubular body 12 positioned at the treatment site 88.

Figure 11D:
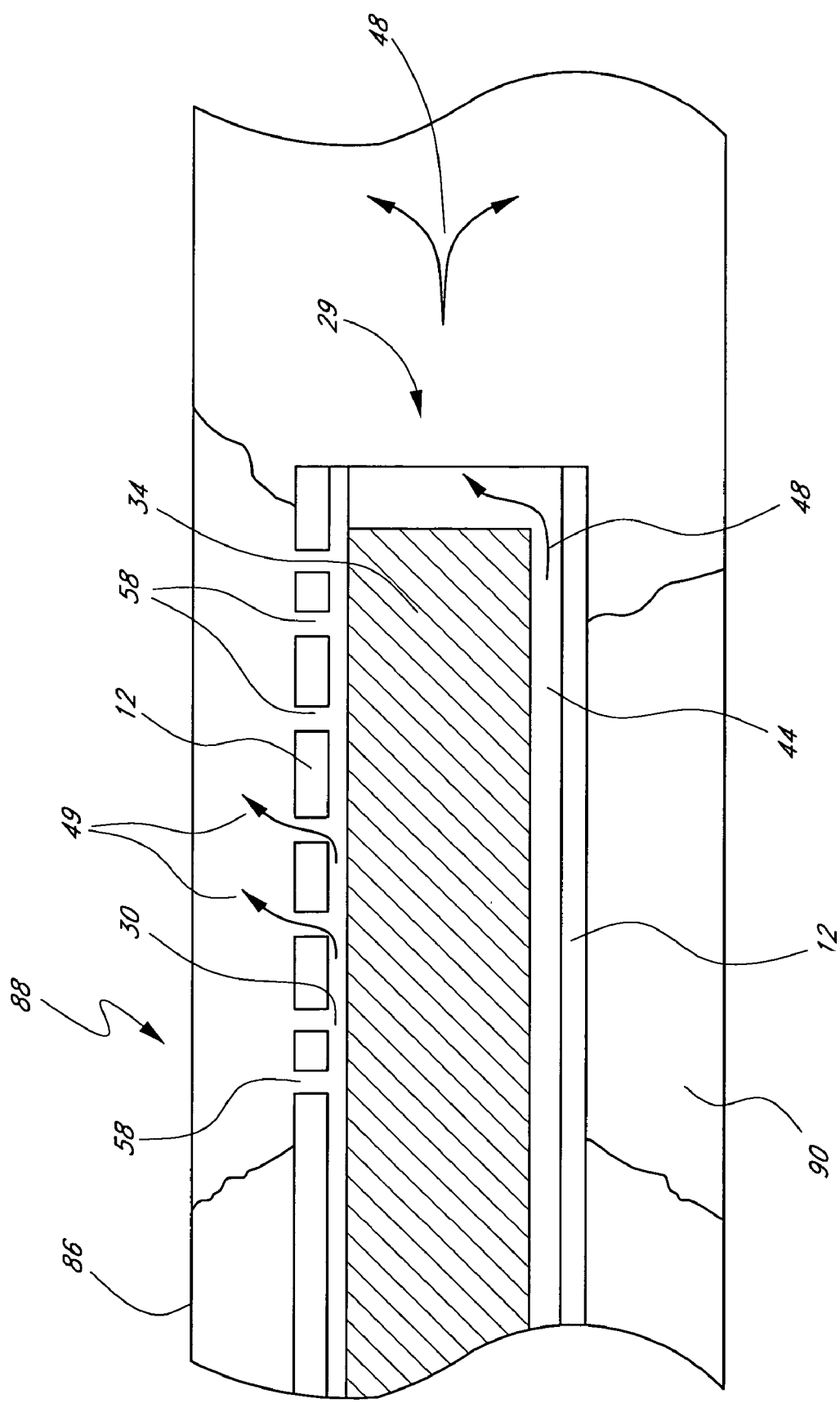
FIG. 11D is a cross-sectional view of the distal end of the ultrasonic catheter of FIG. 11C, wherein an inner core has been inserted into the tubular body to perform a treatment.

As illustrated in FIG. 11D, the inner core 34 is then inserted into the tubular body 12 until the ultrasound assembly is positioned at least partially within the energy delivery section 18 of the tubular body 12. Once the inner core 34 is properly positioned, the ultrasound assembly 42 is activated to deliver ultrasonic energy through the energy delivery section 18 to the clot 90. As described above, in one embodiment, suitable ultrasonic energy is delivered with a frequency between about 20 kHz and about 20 MHz.

In a certain embodiment, the ultrasound assembly 42 comprises sixty ultrasound radiating members 40 spaced over a length between approximately 30 cm and 50 cm. In such embodiments, the catheter 10 can be used to treat an elongate clot 90 without requiring movement of or repositioning of the catheter 10 during the treatment. However, it will be appreciated that in modified embodiments the inner core 34 can be moved or rotated within the tubular body 12 during the treatment. Such movement can be accomplished by maneuvering the proximal hub 37 of the inner core 34 while holding the backend hub 33 stationary.

Referring again to FIG. 11D, arrows 48 indicate that a cooling fluid flows through the cooling fluid lumen 44 and out the distal exit port 29. Likewise, arrows 49 indicate that a therapeutic compound flows through the fluid delivery lumen 30 and out the fluid delivery ports 58 to the treatment site 88.

The cooling fluid can be delivered before, after, during or intermittently with the delivery of ultrasonic energy. Similarly, the therapeutic compound can be delivered before, after, during or intermittently with the delivery of ultrasonic energy. Consequently, the steps illustrated in FIGS. 11A through 11D can be performed in a variety of different orders than as described above. The therapeutic compound and ultrasonic energy are preferably applied until the clot 90 is partially or entirely dissolved. Once the clot 90 has been dissolved to the desired degree, the tubular body 12 and the inner core 34 are withdrawn from the treatment site 88.

Multi-Resonant Ultrasonic Catheter

As described above, in certain medical procedures it is desired to apply ultrasonic energy having several different frequencies to a treatment site. To address this desire, in certain embodiments, an ultrasonic catheter comprises a plurality of ultrasound radiating members disposed along the longitudinal axis of an ultrasonic catheter. In such embodiments, at least two of the ultrasonic elements have different resonant frequencies, thus allowing ultrasonic energy to be applied to the treatment site at different frequencies. The construction of such an ultrasonic catheter is well-suited for the treatment of long segment peripheral arterial occlusions, such as, for example, those in the arteries of the leg.

In such embodiments, a single ultrasonic catheter can be used in a wide variety of treatment applications. Such an ultrasonic catheter also provides the ability to effectively apply different frequencies of ultrasonic energy at a single treatment site. Thus, such an ultrasonic catheter provides convenience and versatility by saving time and eliminating unnecessary redundancy.

As illustrated in FIGS. 1 through 7, and as described above in greater detail, the ultrasonic catheter 10 preferably includes a tubular body 12 provided with a central lumen 51 for receiving an elongate inner core 34. The elongate inner core 34 comprises an elongate common wire 108 that is preferably substantially flat. A plurality of ultrasound radiating members 40 are provided along the elongate common wire 108. The ultrasound radiating members 40 can be positioned along the elongate common wire 108 in variety of different configurations as necessary to suit the needs of a particular application.

As illustrated in FIGS. 5 and 6, and as described above in greater detail, the ultrasound radiating members 40 are preferably electrically connected to adjustable power control circuitry 100. The control circuitry 100 provides an input signal to the ultrasound radiating members 40. In such embodiments, the frequency of the input signal can be adjusted to excite a particular ultrasound radiating member, or group of ultrasound radiating members, at the appropriate resonant frequency. For example, in one embodiment, each of the groups G1 through G5 comprise ultrasound radiating members having a common resonant frequency. The use of a single wire pair, as shown in the wiring arrangement illustrated in FIGS. 5 and 6, advantageously eliminates the need for discrete switching for activating individual ultrasonic elements on the ultrasonic catheter. Furthermore, this configuration simplifies construction and significantly reduces manufacturing costs.

Figure 12:
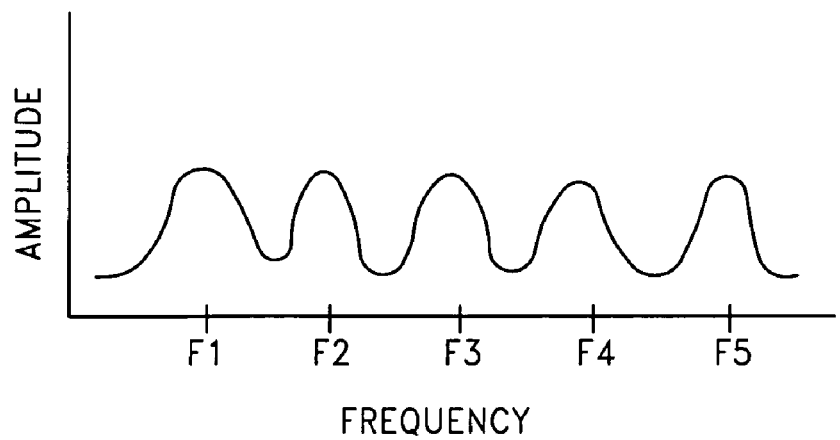
FIG. 12 is a preferred frequency response diagram showing the amplitude output of an ultrasonic catheter as a function of input frequency.

FIG. 12 shows a first preferred frequency response for an ultrasonic catheter with five groups G1 through G5 of ultrasound radiating members, each with a unique resonant frequency. The frequency response shows the output amplitude of ultrasonic energy as a function of input signal frequency. As illustrated, each of the five groups has a different resonant frequency (F1, F2, F3, F4 and F5) wherein the amplitude of the ultrasonic energy output increases significantly when the ultrasound radiating members are excited at one of the five resonant frequencies F1 through F5. When the frequency of the input signal is near one of the five resonant frequencies, only one of the groups is excited, while the other groups output relatively little ultrasonic energy. One of ordinary skill in the art will recognize that the frequency response illustrated in FIG. 12 is merely exemplary; the frequencies and amplitudes can be tailored to suit the needs of any particular application. Furthermore, the number of groups or ultrasound radiating members can be varied according to the needs of a particular application.

Figure 13:
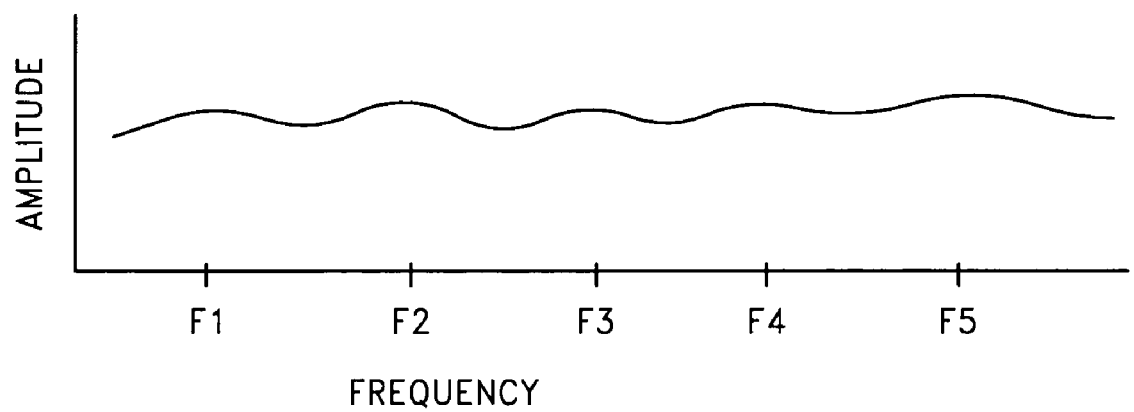
FIG. 13 is another preferred frequency response diagram showing the amplitude output of the ultrasonic catheter as a function of input frequency.

FIG. 13 shows another preferred frequency response wherein the amplitude of the output is nearly constant over a wide range of input signal frequencies. Such a frequency response can be achieved by a variety of techniques, such as, for example, by providing ultrasound radiating members having relatively small separations between the resonant frequencies or by providing ultrasound radiating members that produce ultrasonic energy over a wider range of frequencies.

Figure 14:
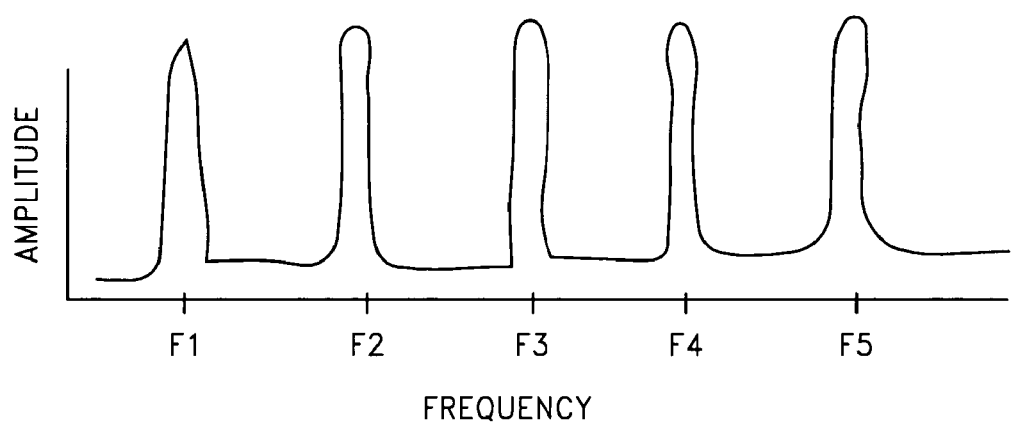
FIG. 14 is another preferred frequency response diagram showing the amplitude output of the ultrasonic catheter as a function of input frequency.

In other embodiments, the ultrasonic catheter comprises ultrasound radiating members exhibiting a narrow frequency response. In such embodiments, the combination of ultrasound radiating members provides a nearly "comb-filter" type of response, as illustrated in FIG. 14. This configuration causes a high output energy to be produced at the input signal frequencies of F1 through F5, while there is relatively little response at other frequencies.

Ultrasonic Catheter Having High Density Clustering of Ultrasound Radiating Members As described above, in certain medical procedures, it is desirable to provide an ultrasonic catheter having a plurality of ultrasound radiating members having a variety of resonant frequencies. For example, multiple ultrasound radiating members can be disposed along the longitudinal axis of a catheter to provide the physician with the ability to emit ultrasonic energy along a substantial length of tissue at a treatment site. In another application, a variety of different types of ultrasound radiating members are disposed at various locations along the catheter for emitting ultrasonic energy at a multitude of different frequencies.

Although the use of multiple ultrasound radiating members on a single catheter has numerous benefits, there are difficulties associated with mounting multiple ultrasound radiating members on a small diameter catheter. For example, one difficulty is caused by the rigidity of ultrasound radiating members. Because ultrasound radiating members have limited flexibility, the overall flexibility of the catheter can be significantly impeded, thereby making the advancement of the catheter through a patient's vasculature extremely difficult and dangerous. Another difficulty is due to the fact that ultrasound radiating members are typically quite large in size and are therefore are not well adapted for use with small catheters.

In response to these and other difficulties, a new and improved ultrasonic catheter has been developed wherein a plurality of ultrasound radiating members are disposed along a catheter in a unique arrangement that does not significantly limit size or impede flexibility. For example, in one preferred embodiment, a plurality of small ultrasound radiating members is provided, wherein the ultrasound radiating members are capable of outputting ultrasonic energy at a variety of different frequencies. In such embodiments, a plurality of ultrasound radiating members is provided along the exterior surface of an elongate inner core. The ultrasound radiating members can be positioned along the inner core in variety of different configurations as necessary to suit a particular need or purpose.

Figure 15A:
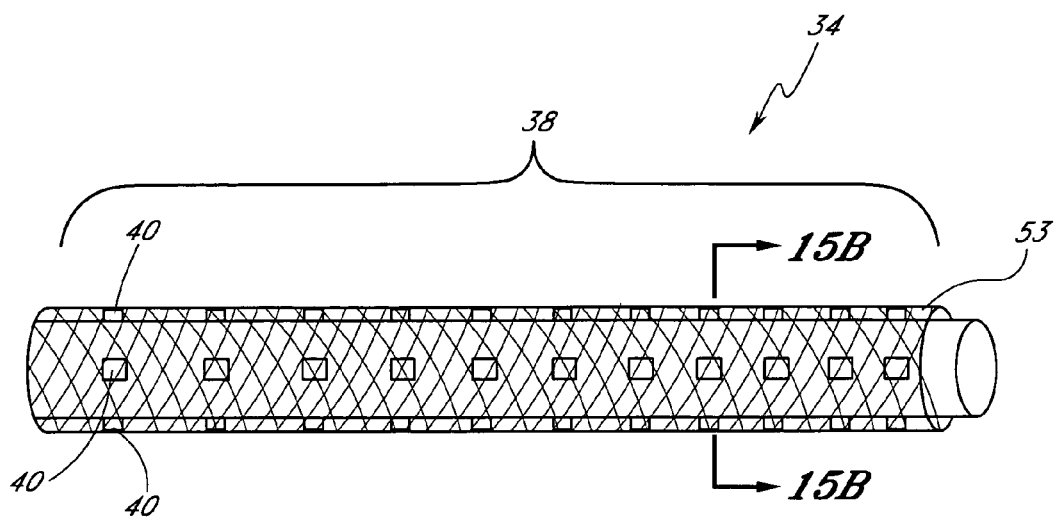
FIG. 15A is a side view of an inner core of an ultrasonic catheter wherein a plurality of ultrasound radiating members are disposed on a conductive wire and covered by a conductive mesh.
Figure 15B:
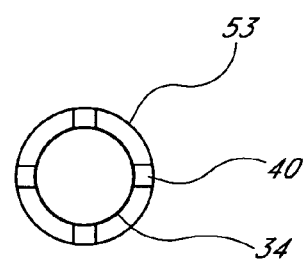
FIG. 15B is a cross-sectional view of the inner core of FIG. 15A.

Referring now to FIG. 15A, one preferred embodiment of an inner core 34 for use with an ultrasonic catheter is illustrated. The inner core 34 generally comprises a distal region 38 and a plurality of ultrasound radiating members 40 disposed along the distal region 38 of the inner core 34. In the illustrated embodiment, the inner core 34 is formed with a substantially circular cross-section, as best shown in FIG. 15B. The ultrasound radiating members 40 are preferably disposed in a high-density formation along the exterior of the inner core 34. In a preferred embodiment, the inner core 34 comprises an electrically conductive material for electrically connecting each of the ultrasound radiating members 40 to a power source (not shown).

Still referring to FIGS. 15A and 15B, in such embodiments a flexible wire mesh 53 preferably surrounds the inner core 34 and ultrasound radiating members 40. The wire mesh 53 is made of an electrically conductive material for conducting electricity and closing the electrical circuit around each of the ultrasound radiating members 40. Preferably, the gaps in the wire mesh 53 are sized to ensure that at least a portion of the wire mesh 53 is always in contact with a top surface of each ultrasound radiating member 40. Both the inner core 34 and the wire mesh 53 preferably have sufficient flexibility such that the catheter has a low resistance to bending thereby facilitating advancement of the catheter through a patient's vasculature. To avoid "shorting" the electrical circuit, the inner core 34 is preferably assembled in a manner such that no direct electrical connection is made between the wire mesh 53 and the inner core 34. This can be achieved by a variety of techniques, such as, for example, by providing electrical insulation in the clearance between the inner core 34 and the wire mesh 53.

Figure 16A:
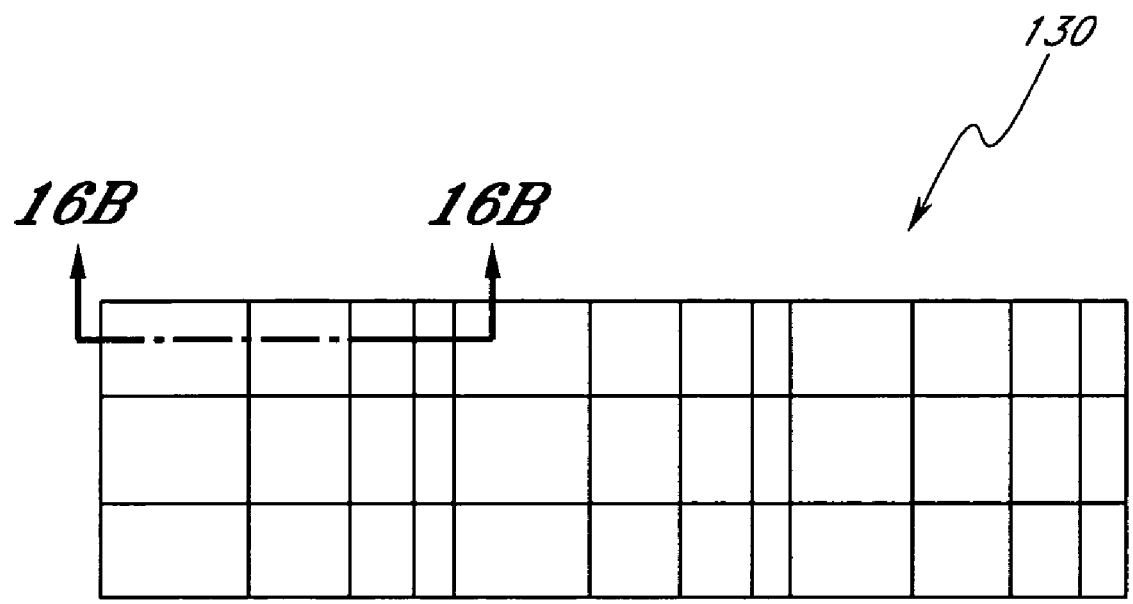
FIG. 16A is a top view of a portion of piezoelectric material showing channels configured to produce a plurality of ultrasound radiating members having different sizes.
Figure 16B:
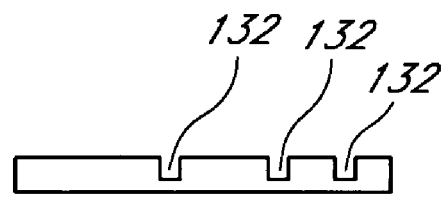
FIG. 16B is a cross-sectional view of the piezoelectric material showing the channels formed therein.

FIG. 16A illustrates a sheet 130 of piezoelectric material which is manufactured to produce a plurality of ultrasound radiating members of varying sizes. As illustrated in FIG. 16B, small channels 132 are formed in the surface of the sheet 130. The channels 132 are spaced to divide the sheet 130 into a plurqality of ultrasound radiating members of varying sizes. For example, in the illustrated embodiment, four sizes of ultrasound radiating members are provided in a repeating pattern. Each size has a different resonant frequency and therefore emits ultrasonic most efficiently at a different input frequency.

Figure 17A:
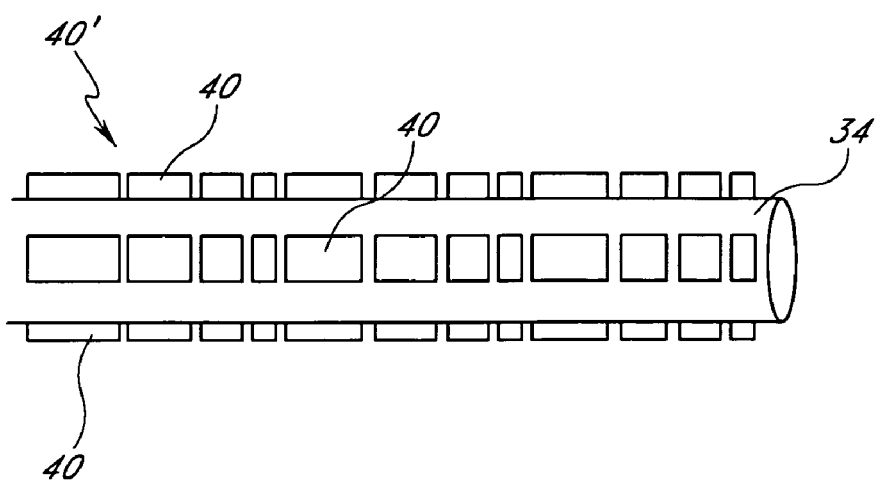
FIG. 17A is a side view of an inner core of an ultrasonic catheter wherein strips of different sized ultrasound radiating members are disposed along the length of an inner core.

FIG. 17A illustrates an inner core 34 having a plurality of ultrasonic strips 40' disposed axially along the inner core 34. Each strip 40' is formed from the sheet 130 described above and illustrated in FIGS. 16A and 16B. Each strip 40' comprises a plurality of ultrasound radiating members 40 disposed in a repeating fashion. In the illustrated embodiment, each ultrasonic strip 40' comprises ultrasound radiating members 40 having four different sizes. The illustrated embodiment includes four strips 40' (three of which are visible in the illustrated side view) provided along the inner core 34 that are equally spaced around the circumference of the inner core 34.

Figure 17B:
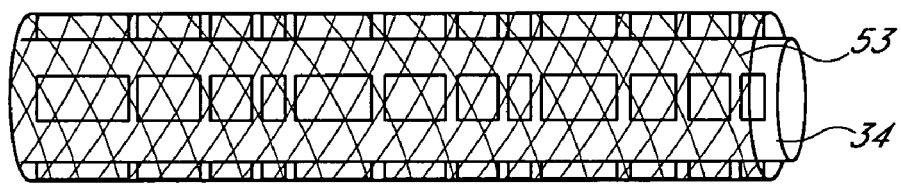
FIG. 17B is a side view of the inner core of FIG. 17A wherein an electrically conductive wire mesh is disposed over the inner core.

FIG. 17B illustrates the inner core of FIG. 17A wherein a wire mesh 53 surrounds the inner core 34 and the strips 40'. At least a portion of the wire mesh 53 contacts each of the strips 40' and provides an electrical connection to a power source (not shown). This configuration essentially connects each of the strips 40' in parallel to the power source. Therefore, a failure of one or more elements will not significantly alter the overall operation of the ultrasonic catheter.

Figure 17C:
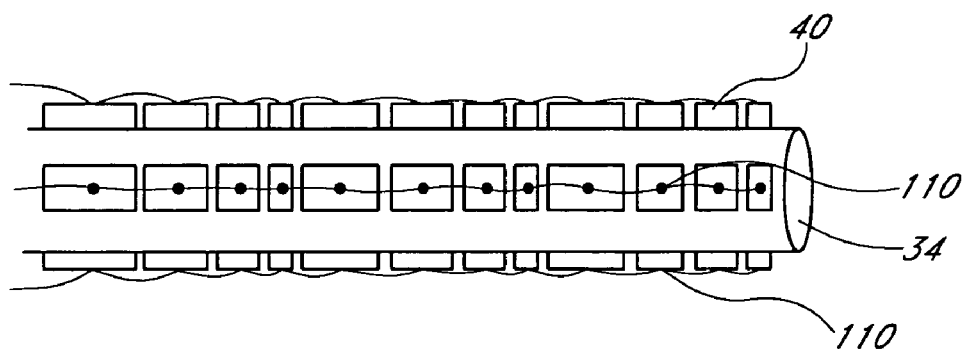
FIG. 17C is a side view of the inner core of FIG. 17A wherein each ultrasound radiating member strip comprises an array of elements electrically connected in parallel by a wire.

FIG. 17C illustrates a modified embodiment wherein each of the strips 40' is connected to the power source by a single lead wire 110. In such embodiments, the single lead wire 110 serves the same function as the wire mesh 53 illustrated in FIG. 17B.

While the foregoing detailed description has described several embodiments of the apparatus and methods of the present invention, it is to be understood that the above description is illustrative only and not limited to the disclosed invention. It will be appreciated that the specific dimensions of the various catheters and inner cores can differ from those described above, and that the methods described can be used within any biological conduit in a patient's body, while remaining within the scope of the present invention. In particular, the methods for evaluating the efficacy of a clot dissolution treatment can be used to evaluate treatments performed with a the peripheral catheter disclosed herein, as well as with the small vessel catheter disclosed in U.S. patent application, entitled "Small Vessel Ultrasound Catheter" and filed Dec. 3, 2002. Thus, the present invention is to be limited only by the claims that follow.

We claim:

1. A catheter system for delivering ultrasonic energy and a therapeutic compound to a treatment site within a patient's vasculature, the system comprising:
    a tubular body having a proximal end, a distal end and an energy delivery section positioned between the proximal end and the distal end;
    an inner core configured for insertion into the tubular body, the inner core having an outer surface and the inner core comprising an electrically conductive core material;
    a plurality of ultrasound radiating members positioned on the outer surface of the inner core, and electrically connected to the electrically conductive core material;
    an electrically conductive tube-shaped member disposed over the inner core and over the ultrasound radiating members positioned thereon, wherein at least a portion of the electrically conductive tube-shaped member is electrically connected to a plurality of the ultrasound radiating members; and
    a control circuitry configured to deliver an input signal to a plurality of the ultrasound radiating members.

2. The system of claim 1, wherein the tube-shaped member comprises a wire mesh.

3. The system of claim 1, wherein the plurality of ultrasound radiating members have a plurality of different resonant frequencies.

4. The system of claim 3, wherein the input signal comprises a multi-frequency input signal including at least one of the resonant frequencies.

5. The system of claim 1, wherein a plurality of strips are disposed on the inner core, each strip comprising a plurality of ultrasound radiating members coupled together.

6. The system of claim 1, further comprising a fluid delivery lumen formed in the tubular body, the fluid delivery lumen having at least one outlet proximal to the ultrasound radiating members.

7. The system of claim 1, further comprising at least one cooling fluid channel positioned between the inner core and the tubular body.

8. The system of claim 1, wherein the enemy delivery section has a length in the range of between approximately 5 cm and 70 cm.

9. A ultrasonic catheter comprising:
    an elongate tubular body having a hollow central lumen, a proximal end and a distal; and
    an inner core configured for insertion into the hollow central lumen, the inner core comprising a common wire and a plurality of ultrasound radiating members, wherein the plurality of ultrasound radiating members are mounted on the common wire, and wherein at least two of the ultrasound radiating members have a different resonant frequency.

10. The catheter of claim 9, further comprising control circuitry configured to provide an input signal to at least some of the ultrasound radiating members.

11. The catheter of claim 10, wherein the plurality of ultrasound radiating members have a plurality of different resonant frequencies.

12. The catheter of claim 11, wherein the input signal comprises a multi-frequency input signal including at least one of the resonant frequencies.

13. The catheter of claim 9, further comprising a fluid delivery lumen formed in the, tubular body, the fluid delivery lumen having at least one outlet proximal to the ultrasound radiating members.

14. The catheter of claim 9, wherein a portion of the hollow central lumen functions as a cooling fluid lumen.

15. The catheter of claim 9, further comprising an electrically conductive tube-shaped member disposed over the inner core, wherein at least a portion of the electrically conductive tube-shaped member is electrically connected to a plurality of the ultrasound radiating members.

16. The catheter of claim 15, wherein the tube-shaped member comprises a wire mesh.

17. The catheter of claim 9, wherein a plurality of strips are disposed on the inner core, each strip comprising a plurality of ultrasound radiating members coupled together.

18. The catheter of claim 9, wherein a distance between a most proximal ultrasound radiating member and a most distal ultrasound radiating member is between approximately 5 cm and 70 cm.

19. A method comprising:
    positioning an ultrasonic catheter at a treatment site within a patient's vasculature, the ultrasonic catheter having en elongate inner core with a plurality of ultrasound radiating members disposed thereon, the ultrasound radiating members having a plurality of resonant frequencies; and
    delivering a multi-frequency driving signal to the plurality of ultrasound radiating members, wherein the frequencies comprising the multi-frequency driving signal include at least one of the resonant frequencies.

20. The method of claim 19, further comprising:
    delivering a therapeutic compound to the treatment site concurrent with the delivery of the multi-frequency driving signal to the plurality of ultrasound radiating members.

21. The method of claim 19, further comprising passing a cooling fluid over at least a portion of the inner core.

22. The method of claim 19, wherein the frequencies comprising the multi-frequency driving signal include a plurality of the resonant frequencies.

23. The method of claim 19, wherein the frequencies comprising the multi-frequency driving signal vary with time, such that a first subset of ultrasound radiating members emit ultrasonic energy during a first treatment period, and a second subset of ultrasound radiating members emit ultrasonic energy during a second treatment period.

24. The method of claim 23, wherein the first subset of ultrasound radiating members are grouped in a first region on the elongate inner core, and the second subset of ultrasound radiating members are grouped in a second region on the elongate inner core, the first region spatially separated from the second region.

25. The method of claim 19, wherein an electrically conductive tube-shaped member is disposed over the inner core, and wherein at least a portion of the electrically conductive tube-shaped member is electrically connected to a plurality of the ultrasound radiating members.

26. The method of claim 25, wherein the tube-shaped member comprises a wire mesh.

27. The method of claim 19, wherein a plurality of strips are disposed on the inner core, each strip comprising a plurality of ultrasound radiating members coupled together.

* * * * *

UNITED STATES PATENT AND TRADEMARK OFFICE
CERTIFICATE OF CORRECTION

| | |
|---|---|
| PATENT NO. | : 6,958,040 B2 |
| APPLICATION NO. | : 10/331439 |
| DATED | : October 25, 2005 |
| INVENTOR(S) | : Leonard R. Oliver et al. |

It is certified that error appears in the above-identified patent and that said Letters Patent is hereby corrected as shown below:

At Col. 19, Line 65, in Claim 8, delete "enemy" and insert -- energy --, therefor.

At Col. 20, Line 3, in Claim 9, delete "distal;" and insert -- distal end; --, therefor.

At Col.20, Line 21, in Claim 13, delete "the, tubular" and insert -- the tublar --, therefor.

At Col. 20, Line 43, in Claim 19, delete "en" and insert -- an --, therefor.

Signed and Sealed this

Twenty-seventh Day of March, 2007

JON W. DUDAS
*Director of the United States Patent and Trademark Office*

UNITED STATES PATENT AND TRADEMARK OFFICE
CERTIFICATE OF CORRECTION

PATENT NO. : 6,958,040 B2 Page 1 of 1
APPLICATION NO. : 10/331439
DATED : October 25, 2005
INVENTOR(S) : Leonard R. Oliver et al.

It is certified that error appears in the above-identified patent and that said Letters Patent is hereby corrected as shown below:

Column 1, line 15, the following header and paragraph should be inserted:

STATEMENT REGARDING FEDERALLY SPONSORED R&D

The invention was made with government support under Grant No. NIH R44 HL057739 awarded by the National Institutes of Health. The government has certain rights in the invention.

Signed and Sealed this

First Day of July, 2008

JON W. DUDAS
*Director of the United States Patent and Trademark Office*